(12) United States Patent
Bubb et al.

(10) Patent No.: US 6,951,553 B2
(45) Date of Patent: Oct. 4, 2005

(54) TISSUE CLOSURE TREATMENT SYSTEM AND METHOD WITH EXTERNALLY-APPLIED PATIENT INTERFACE

(75) Inventors: Stephen K. Bubb, Kansas City, MO (US); David S. Zamierowski, Overland Park, KS (US)

(73) Assignee: KCI Licensing, Inc, San Antonio, TX (US)

( * ) Notice: Subject to any disclaimer, the term of this patent is extended or adjusted under 35 U.S.C. 154(b) by 248 days.

(21) Appl. No.: 10/334,766

(22) Filed: Dec. 31, 2002

(65) Prior Publication Data

US 2004/0127862 A1 Jul. 1, 2004

(51) Int. Cl.$^7$ .......................... A61M 1/00; A61M 27/00; A61M 7/00
(52) U.S. Cl. ..................... 604/327; 604/541; 604/543; 604/268; 601/6
(58) Field of Search ............................... 604/289, 290, 604/304, 313, 540, 541, 543, 327, 268; 601/6

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,969,057 A | 1/1961 | Simmons |
| 3,115,138 A | 12/1963 | MCEvenny et al. |
| 3,367,332 A | 2/1968 | Groves |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez |

(Continued)

OTHER PUBLICATIONS

The Woodpecker, promotional literature for product manufactured by IMT (Integral Medizintechnik) and distributed by Minnestota Bramstedt Surgical, Inc.; Availabe at web site: www.mnbramstedt.com.

(Continued)

Primary Examiner—Larry I. Schwartz
Assistant Examiner—Michael G. Bogart
(74) Attorney, Agent, or Firm—Mark E. Brown

(57) ABSTRACT

A tissue closure treatment system and method are provided with an external patient interface. A first fluid transfer component FTC.1 comprises a strip of porous material, such as rayon, with liquid wicking properties. FTC.1 can be placed directly on a suture line for transferring fluid exuded therethrough. An underdrape is placed over FTC.1 and includes a slot exposing a portion of same. FTC.2 comprises a suitable hydrophobic foam material, such as polyurethane ether, and is placed over the underdrape slot in communication with FTC.1. Negative pressure is applied to FTC.2 through a connecting fluid transfer component FTC.3. A negative pressure source can comprises a manual device or a power-operated suction device. The tissue closure method includes a manual operating mode using a manual suction device with an automatic shut off for discontinuing suction when a predetermined volume of fluid has been drained. An automatic operating mode utilizes a microprocessor, which can be preprogrammed to respond to various patient and operating conditions. The method proceeds through several phases with different components in place and different patient interface functions occurring in each.

35 Claims, 20 Drawing Sheets

U.S. PATENT DOCUMENTS

| | | | |
|---|---|---|---|
| 4,165,748 A | | 8/1979 | Johnson |
| 4,245,630 A | | 1/1981 | Lloyd et al. |
| 4,248,232 A | | 2/1981 | Engelbrecht et al. |
| 4,261,363 A | | 4/1981 | Russo |
| 4,275,721 A | | 6/1981 | Olson |
| 4,297,995 A | | 11/1981 | Golub |
| 4,333,468 A | | 6/1982 | Geist |
| 4,373,519 A | | 2/1983 | Errade et al. |
| 4,382,441 A | | 5/1983 | Svedman |
| 4,392,853 A | | 7/1983 | Muto |
| 4,392,858 A | | 7/1983 | George et al. |
| 4,419,093 A | * | 12/1983 | Deaton ........................ 604/540 |
| 4,419,097 A | | 12/1983 | Rowland |
| 4,475,909 A | | 10/1984 | Eisenberg |
| 4,480,638 A | * | 11/1984 | Schmid ........................ 602/53 |
| 4,525,166 A | * | 6/1985 | Leclerc ........................ 604/133 |
| 4,540,412 A | | 9/1985 | Van Overloop |
| 4,543,100 A | | 9/1985 | Brodsky |
| 4,551,139 A | | 11/1985 | Plaas et al. |
| 4,569,348 A | | 2/1986 | Hasslinger |
| 4,605,339 A | | 8/1986 | Bullivant |
| 4,608,041 A | | 8/1986 | Nielsen |
| 4,640,688 A | | 2/1987 | Hauser |
| 4,655,754 A | | 4/1987 | Richmond |
| 4,733,659 A | | 3/1988 | Edenbaum . |
| 4,743,232 A | | 5/1988 | Kruger |
| 4,787,888 A | | 11/1988 | Fox |
| 4,826,949 A | | 5/1989 | Stanko |
| 4,828,546 A | | 5/1989 | McNeil et al. |
| 4,838,883 A | | 6/1989 | Matsuura |
| 4,840,187 A | | 6/1989 | Brazier |
| 4,863,449 A | | 9/1989 | Therriault et al. |
| 4,872,450 A | | 10/1989 | Austad |
| 4,878,901 A | | 11/1989 | Sachse |
| 4,897,081 A | | 1/1990 | Poirier et al. |
| 4,906,233 A | | 3/1990 | Moriuchi et al. |
| 4,906,240 A | | 3/1990 | Reed et al. |
| 4,919,654 A | | 4/1990 | Kait |
| 4,941,882 A | | 7/1990 | Ward et al. |
| 4,953,565 A | | 9/1990 | Tachibana et al. |
| 4,969,880 A | | 11/1990 | Zamierowski |
| 4,985,019 A | | 1/1991 | Michelson |
| 5,007,936 A | | 4/1991 | Woolson |
| 5,019,083 A | | 5/1991 | Klapper et al. |
| 5,037,397 A | | 8/1991 | Kalt et al. |
| 5,045,054 A | | 9/1991 | Hood et al. |
| 5,100,396 A | | 3/1992 | Zamierowski |
| 5,112,338 A | | 5/1992 | Anspach, III |
| 5,149,331 A | | 9/1992 | Ferdman et al. |
| 5,167,613 A | | 12/1992 | Karami et al. |
| 5,169,399 A | | 12/1992 | Ryland et al. |
| 5,176,663 A | | 1/1993 | Svedman et al. |
| D337,639 S | | 7/1993 | Beckman |
| 5,261,893 A | | 11/1993 | Zamierowski |
| 5,291,887 A | * | 3/1994 | Stanley et al. .............. 600/573 |
| 5,298,015 A | | 3/1994 | Komatsuzaki et al. |
| 5,318,570 A | | 6/1994 | Hood et al. |
| 5,344,415 A | | 9/1994 | Debusk et al. |
| 5,358,494 A | | 10/1994 | Svedman |
| 5,437,651 A | * | 8/1995 | Todd et al. .................. 604/313 |
| 5,507,833 A | | 4/1996 | Bohn |
| 5,522,901 A | | 6/1996 | Thomas et al. |
| D372,309 S | | 7/1996 | Heldreth |
| 5,556,375 A | | 9/1996 | Ewall |
| 5,580,353 A | | 12/1996 | Mendes et al. |
| 5,607,388 A | | 3/1997 | Ewall |
| 5,630,819 A | | 5/1997 | Ashby et al. |
| 5,636,643 A | | 6/1997 | Argenta et al. |
| 5,645,081 A | | 7/1997 | Argenta et al. |
| 5,716,360 A | | 2/1998 | Baldwin et al. |
| 5,738,686 A | | 4/1998 | Kudein-Meesenburg |
| 5,785,700 A | | 7/1998 | Olson |
| 5,800,546 A | | 9/1998 | Marik et al. |
| 5,846,244 A | | 12/1998 | Cripe |
| 5,911,222 A | * | 6/1999 | Lawrence et al. .......... 600/574 |
| 5,921,972 A | * | 7/1999 | Skow .......................... 604/313 |
| 6,071,267 A | * | 6/2000 | Zamierowski .............. 604/289 |
| 6,113,618 A | | 9/2000 | Nic |
| 6,126,659 A | | 10/2000 | Wack |
| 6,146,423 A | | 11/2000 | Cohen et al. |
| 6,159,246 A | | 12/2000 | Mendes et al. |
| 6,174,306 B1 | * | 1/2001 | Fleischmann ................ 604/543 |
| 6,179,804 B1 | * | 1/2001 | Satterfield .................... 604/23 |
| 6,190,391 B1 | | 2/2001 | Stubbs |
| 6,190,392 B1 | | 2/2001 | Vandewalle et al. |
| RE37,358 E | | 9/2001 | Del Rio et al. |
| 6,355,215 B1 | | 3/2002 | Poggie et al. |
| 6,377,653 B1 | | 4/2002 | Lee et al. |
| 6,398,767 B1 | * | 6/2002 | Fleischmann ................ 604/313 |
| 6,430,427 B1 | | 8/2002 | Lee et al. |
| 6,500,209 B1 | | 12/2002 | Kolb |
| 6,503,281 B1 | | 1/2003 | Mallory |
| 6,626,891 B2 | * | 9/2003 | Ohmstede .................... 604/543 |
| 6,685,681 B2 | * | 2/2004 | Lockwood et al. .......... 604/305 |
| 6,695,823 B1 | * | 2/2004 | Lina et al. .................... 604/304 |
| 6,752,794 B2 | * | 6/2004 | Lockwood et al. .......... 604/313 |
| 6,800,074 B2 | * | 10/2004 | Henley et al. ................ 604/319 |
| 2002/0099447 A1 | | 7/2002 | Mears et al. |
| 2002/0116067 A1 | | 8/2002 | Mears et al. |
| 2002/0183565 A1 | | 12/2002 | Ansmann |
| 2003/0050594 A1 | * | 3/2003 | Zamierowski ................ 604/46 |
| 2003/0097135 A1 | | 5/2003 | Panenberg |
| 2004/0039415 A1 | * | 2/2004 | Zamierowski ................ 606/215 |

OTHER PUBLICATIONS

Halkey–Roberts, St. Petersburg, Florida, Pocket Pump Assembly, Drawing dated Jul. 21, 1997. Available web site: www.halkey–roberts.com/showpic.asp?filename=V15500PPXMED.jpg, Acessed on Nov. 18, 2002.

Haemonetics:Products and Programs–OrthoPAT System, Availabel web site: www.haemonetics.com/site/content/products/. . . Accessed on Nov. 28, 2002.

PCT International Search Report; Application PCT/US03/41667, Stephen K. Bubb et al., Tissue Closure Treatment System, Patient Interface and Method.

* cited by examiner

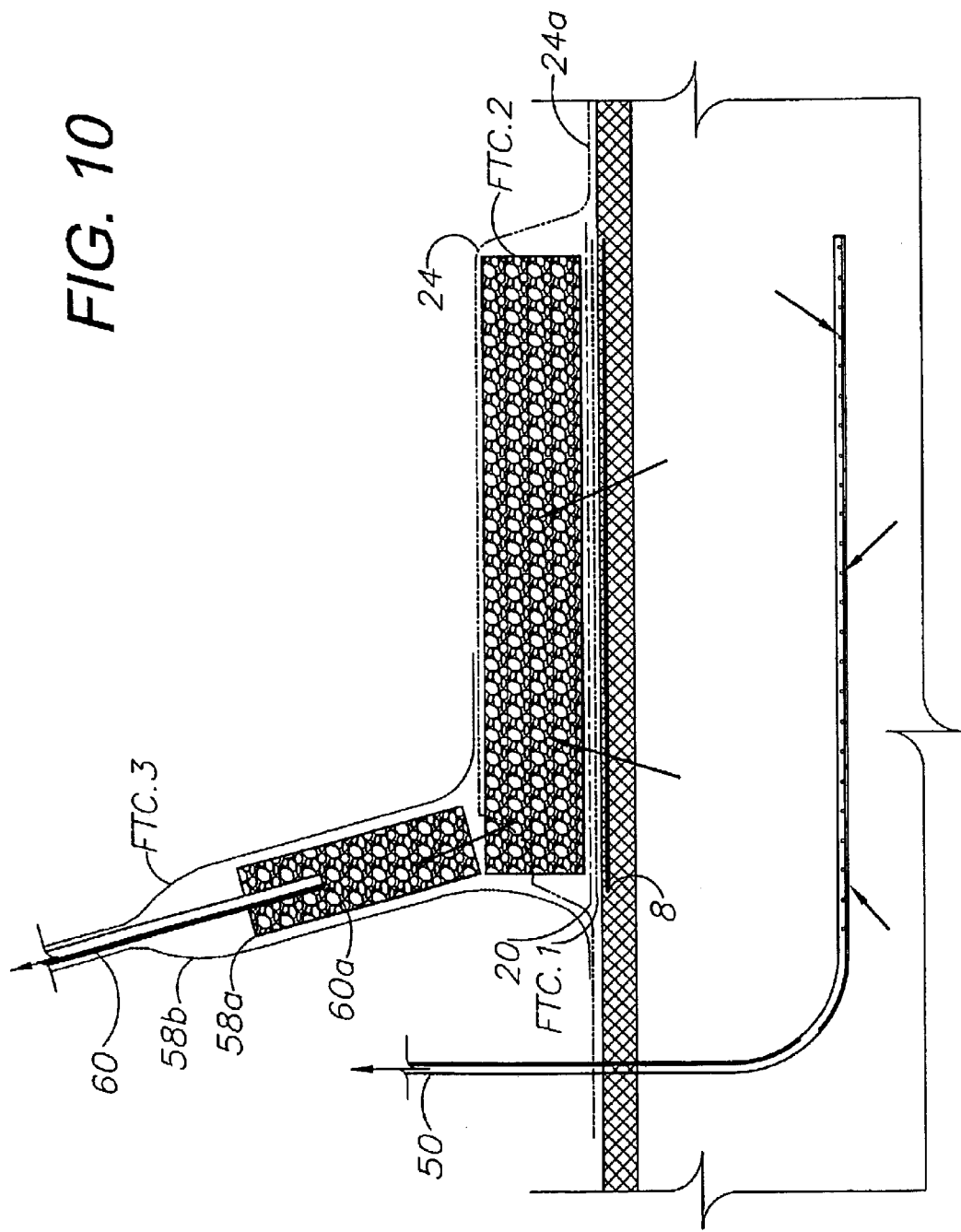

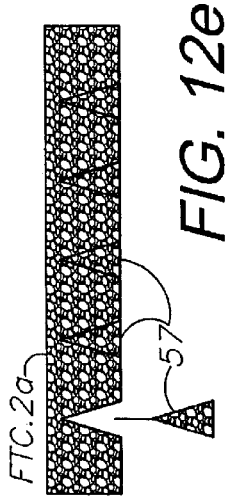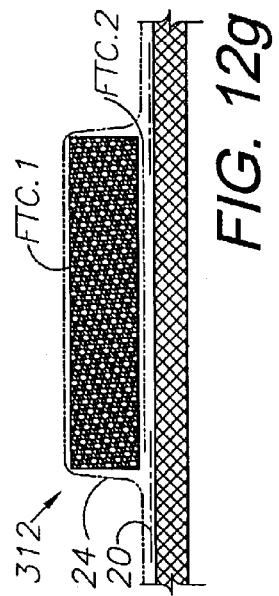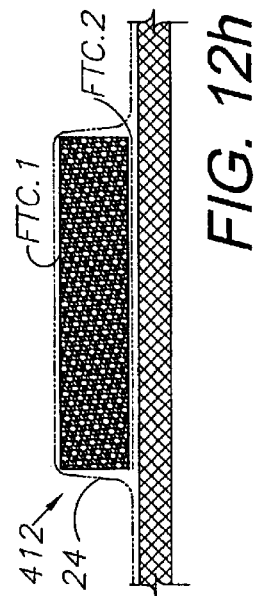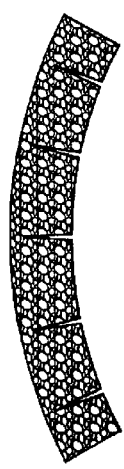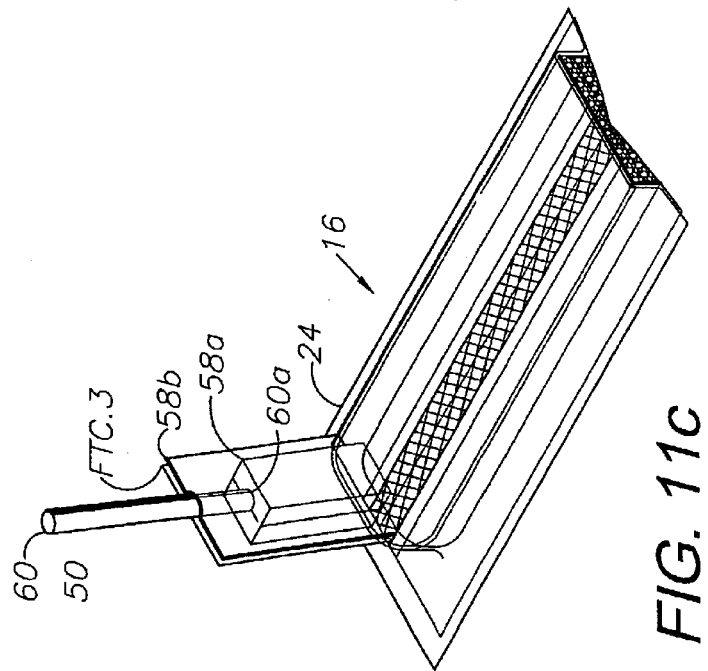

TISSUE CLOSURE TREATMENT SYSTEM AND METHOD WITH EXTERNALLY-APPLIED PATIENT INTERFACE

BACKGROUND OF THE INVENTION

1. Field of the Invention

The present invention relates generally to medical devices and methods for treating closed wounds and incisions, and in particular to a system and method for draining and/or irrigating tissue separations, such as surgical incisions, and for compressing and stabilizing a dissected or traumatized field with ambient air pressure created by an external patient interface component and a vacuum source.

2. Description of the Related Art

Tissue separations can result from surgical procedures and other causes, such as traumatic and chronic wounds. Various medical procedures are employed to close tissue separations. An important consideration relates to securing separate tissue portions together in order to promote closure and healing. Incisions and wounds can be closed with sutures, staples and other medical closure devices. The "first intention" (primary intention healing) in surgery is to "close" the incision. For load-bearing tissues, such as bone, fascia, and muscle, this requires substantial material, be it suture material, staples, or plates and screws. For the wound to be "closed," the epithelial layer must seal. To accomplish this, the "load bearing" areas of the cutaneous and subcutaneous layers (i.e., the deep dermal elastic layer and the superficial fascia or fibrous layers of the adipose tissue, respectively) must also at least be held in approximation long enough for collagen deposition to take place to unite the separated parts.

Other important considerations include controlling bleeding, reducing scarring, eliminating the potential of hematoma, seroma, and "dead-space" formation and managing pain. Dead space problems are more apt to occur in the subcutaneous closure. Relatively shallow incisions can normally be closed with surface-applied closure techniques, such as sutures, staples, glues and adhesive tape strips. However, deeper incisions may well require not only skin surface closure, but also time-consuming placement of multiple layers of sutures in the load-bearing planes.

Infection prevention is another important consideration. Localized treatments include various antibiotics and dressings, which control or prevent bacteria at the incision or wound site. Infections can also be treated and controlled systemically with suitable antibiotics and other pharmacologics.

Other tissue-separation treatment objectives include minimizing the traumatic and scarring effects of surgery and minimizing edema. Accordingly, various closure techniques, postoperative procedures and pharmacologics are used to reduce postoperative swelling, bleeding, seroma, infection and other undesirable, postoperative side effects. Because separated tissue considerations are so prevalent in the medical field, including most surgeries, effective, expedient, infection-free and aesthetic tissue closure is highly desirable from the standpoint of both patients and health-care practitioners. The system, interface and method of the present invention can thus be widely practiced and potentially provide widespread benefits to many patients.

Fluid control considerations are typically involved in treating tissue separations. For example, subcutaneous bleeding occurs at the fascia and muscle layers in surgical incisions. Accordingly, deep drain tubes are commonly installed for the purpose of draining such incisions. Autotransfusion has experienced increasing popularity in recent years as equipment and techniques for reinfusing patients' whole blood have advanced considerably. Such procedures have the advantage of reducing dependence on blood donations and their inherent risks. Serous fluids are also-typically exuded from incision and wound sites and require drainage and disposal. Fresh incisions and wounds typically exude blood and other fluids at the patient's skin surface for several days during initial healing, particularly along the stitch and staple lines along which the separated tissue portions are closed.

Another area of fluid control relates to irrigation. Various irrigants are supplied to separated tissue areas for countering infection, anesthetizing, introducing growth factors and otherwise promoting healing. An effective fluid control system preferably accommodates both draining and irrigating functions sequentially or simultaneously.

Common orthopedic surgical procedures include total joint replacements (TJRs) of the hip, knee, elbow, shoulder, foot and other joints. The resulting tissue separations are often subjected to flexure and movement associated with the articulation of the replacement joints. Although the joints can be immobilized as a treatment option, atrophy and stiffness tend to set in and prolong the rehabilitation period. A better option is to restore joint functions as soon as possible. Thus, an important objective of orthopedic surgery relates to promptly restoring to patients the maximum use of their limbs with maximum ranges of movement.

Similar considerations arise in connection with various other medical procedures. For example, arthrotomy, reconstructive and cosmetic procedures, including flaps and scar revisions, also require tissue closures and are often subjected to movement and stretching. Other examples include incisions and wounds in areas of thick or unstable subcutaneous tissue, where splinting of skin and subcutaneous tissue might reduce dehiscence of deep sutures. The demands of mobilizing the extremity and the entire patient conflict with the restrictions of currently available methods of external compression and tissue stabilization. For example, various types of bandage wraps and compressive hosiery are commonly used for these purposes, but none provides the advantages and benefits of the present invention The aforementioned procedures, as well as a number of other applications discussed below, can benefit from a tissue-closure treatment system and method with a surface-applied patient interface for fluid control and external compression.

Postoperative fluid drainage can be accomplished with various combinations of tubes, sponges, and porous materials adapted for gathering and draining bodily fluids. The prior art includes technologies and methodologies for assisting drainage. For example, the Zamierowski U.S. Pat. Nos. 4,969,880; 5,100,396; 5,261,893; 5,527,293; and 6,071,267 disclose the use of pressure gradients, i.e., vacuum and positive pressure, to assist with fluid drainage from wounds, including surgical incision sites. Such pressure gradients can be established by applying porous sponge material either internally or externally to a wound, covering same with a permeable, semi-permeable, or impervious membrane, and connecting a suction vacuum source thereto. Fluid drawn from the patient is collected for disposal. Such fluid control methodologies have been shown to achieve significant improvements in patient healing. Another aspect of fluid management, postoperative and otherwise, relates to the application of fluids to wound sites for purposes of irrigation, infection control, pain control, growth factor application, etc. Wound drainage devices are also used to achieve fixation and immobility of the tissues, thus aiding healing and closure. This can be accomplished by both internal closed wound drainage and external, open-wound vacuum devices applied to the wound surface. Fixation of tissues in apposition can also be achieved by bolus tie-over dressings (Stent dressings), taping, strapping and (contact) casting.

Heretofore there has not been available a tissue closure system, patient interface and method with the advantages and features of the present invention.

SUMMARY OF THE INVENTION

In the practice of the present invention, a system and method are provided for enhancing closure of separated tissue portions using a surface-applied patient interface. Subsurface drainage, irrigation and autotransfusion components can optionally be used in conjunction with the surface-applied, external interface. The external interface can be advantageously placed over a stitch or staple line and includes a primary transfer component comprising a strip of porous material, such as rayon, applied directly to the patient for wicking or transferring fluid to a secondary transfer component comprising a sponge or foam material. An underdrape is placed between the transfer elements for passing fluid therebetween through an underdrape opening, such as a slot. An overdrape is placed over the secondary transfer component and the surrounding skin surface. The patient interface is connected to a negative pressure source, such as a vacuum assisted closure device, wall suction or a mechanical suction pump. A manual control embodiment utilizes a finite capacity fluid reservoir with a shut-off valve for discontinuing drainage when a predetermined amount of fluid is collected. An automatic control embodiment utilizes a microprocessor, which is adapted for programming to respond to various inputs in controlling the operation of the negative pressure source. A closed wound or incision treatment method of the present invention involves three phases of fluid control activity, which correspond to different stages of the healing process. In a first phase active drainage is handled. In a second phase components can be independently or sequentially disengaged. In a third phase the secondary transfer component can optionally be left in place for protection and to aid in evacuating any residual fluid from the suture/staple line through the primary transfer component.

BRIEF DESCRIPTION OF THE DRAWINGS

The drawings constitute a part of this specification and include exemplary embodiments of the present invention and illustrate various objects and features thereof.

FIG. 10 is a cross-sectional view thereof, taken generally along line 10—10 in FIG. 9 and particularly showing FTC.3.

FIG. 11c is a perspective view of a patient interface adapted for prepackaging, application to a patient and connection to a negative pressure source.

FIGS. 12e,f show a modified FTC.2a with removable wedges to facilitate articulation, such as flexure of a patient joint.

FIGS. 12g,h show alternative embodiment external patient interface assemblies.

DETAILED DESCRIPTION OF THE PREFERRED EMBODIMENTS

I. Introduction and Environment

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

II. Tissue Closure System 2

Figure 1:
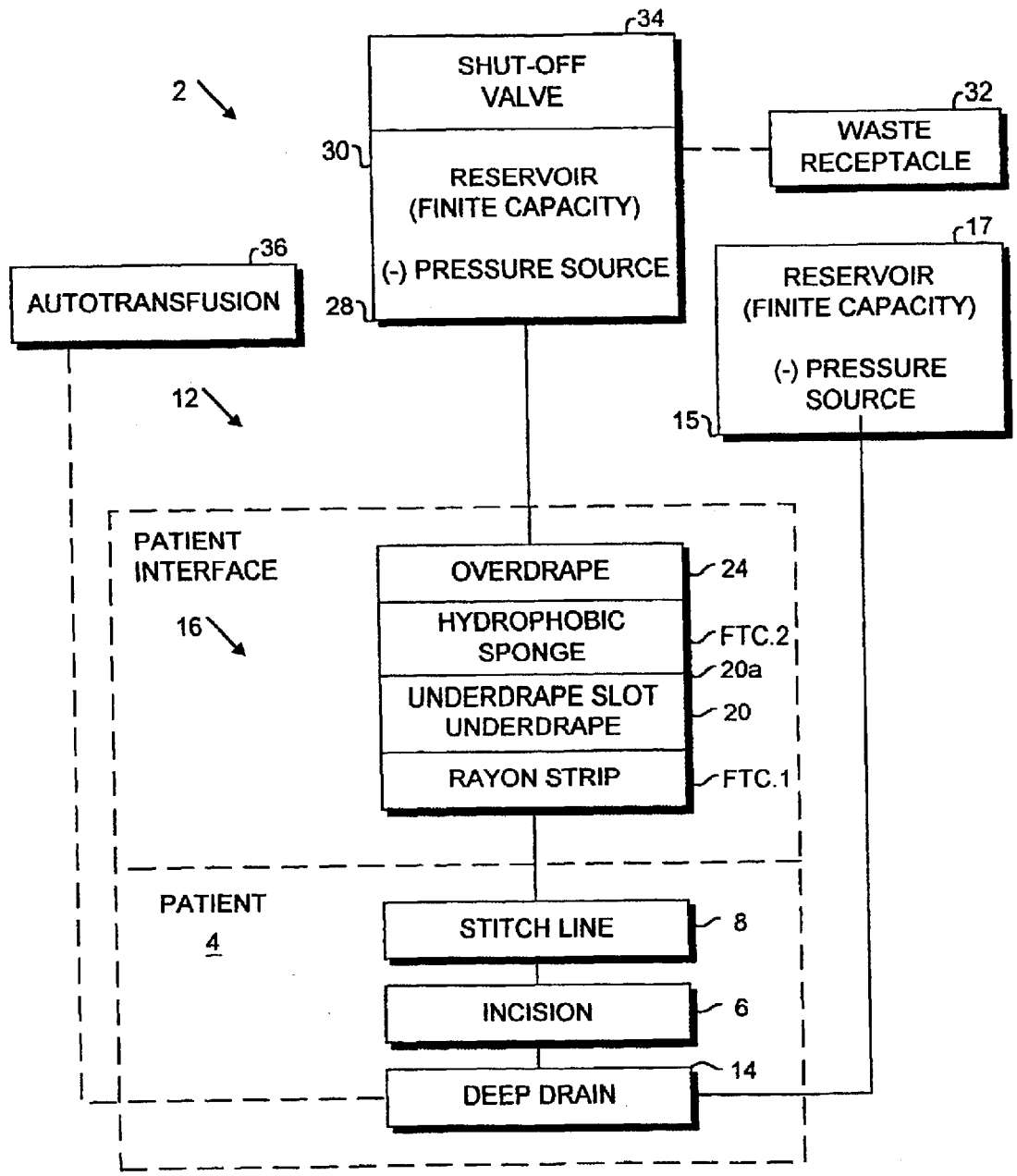
FIG. 1 is a schematic, block diagram of a tissue closure treatment and system embodying the present invention.

Referring to the drawings in more detail, the reference numeral 2 generally designates a tissue closure treatment system embodying the present invention. As shown in FIG. 1, the system 2 is adapted for use on a patient 4 with an incision or wound 6, which can be closed by a stitch line 8 consisting of sutures 10, staples or other suitable medical fasteners.

A patient interface 12 consists of an optional deep drain 14 connected to a deep drain negative pressure source 15 associated with a deep drainage reservoir 17 and an external patient interface 16 including a primary fluid transfer component FTC.1 comprising a strip of rayon or other suitable porous material, an underdrape 20 generally covering FTC.1 and including a slot 20a, a secondary fluid transfer component FTC.2 comprising a hydrophobic sponge and an overdrape 24.

A fluid handling subsystem 26 includes the deep drain negative pressure source 15 and a surface drain negative pressure source 28, which can be combined for applications where a common negative pressure source and a collection receptacle are preferred. The negative pressure sources 15, 28 can operate either manually or under power. Examples of both types are well-known in the medical art. For example, a manually operable portable vacuum source (MOPVS) is shown in U.S. Pat. No. 3,115,138, which is incorporated herein by reference. The MOPVS is available from Zimmer, Inc. of Dover, Ohio under the trademark HEMOVAC®. Bulb-type actuators, such as that shown in U.S. Pat. No. 4,828,546 (incorporated herein by reference) and available from Surgidyne, Inc. of Eden Prairie, Minn., can be used on smaller wounds, for shorter durations or in multiples. Moreover, power-actuated vacuum can be provided by vacuum assisted closure equipment available under the trademark THE VAC® from Kinetic Concepts, Inc. of San Antonio, Tex. Still further, many health-care facilities, particularly hospitals and clinics, are equipped with suction systems with sources of suction available at wall-mounted outlets.

A finite capacity reservoir 30 is fluidically connected to the negative pressure source 28 and is adapted to discharge to a waste receptacle 32. A shut-off valve 34 is associated with the reservoir 30 and is adapted to automatically discontinue drainage when the reservoir 30 is filled to a predetermined volume.

An optional autotransfusion subsystem 36 can be connected to the deep drain 14 and is adapted for reinfusing the patient 4 with his or her own blood. U.S. Pat. No. 5,785,700 discloses such an autotransfusion system with a portable detachable vacuum source, which is available from Zimmer, Inc. and is incorporated herein by reference.

Figure 2:
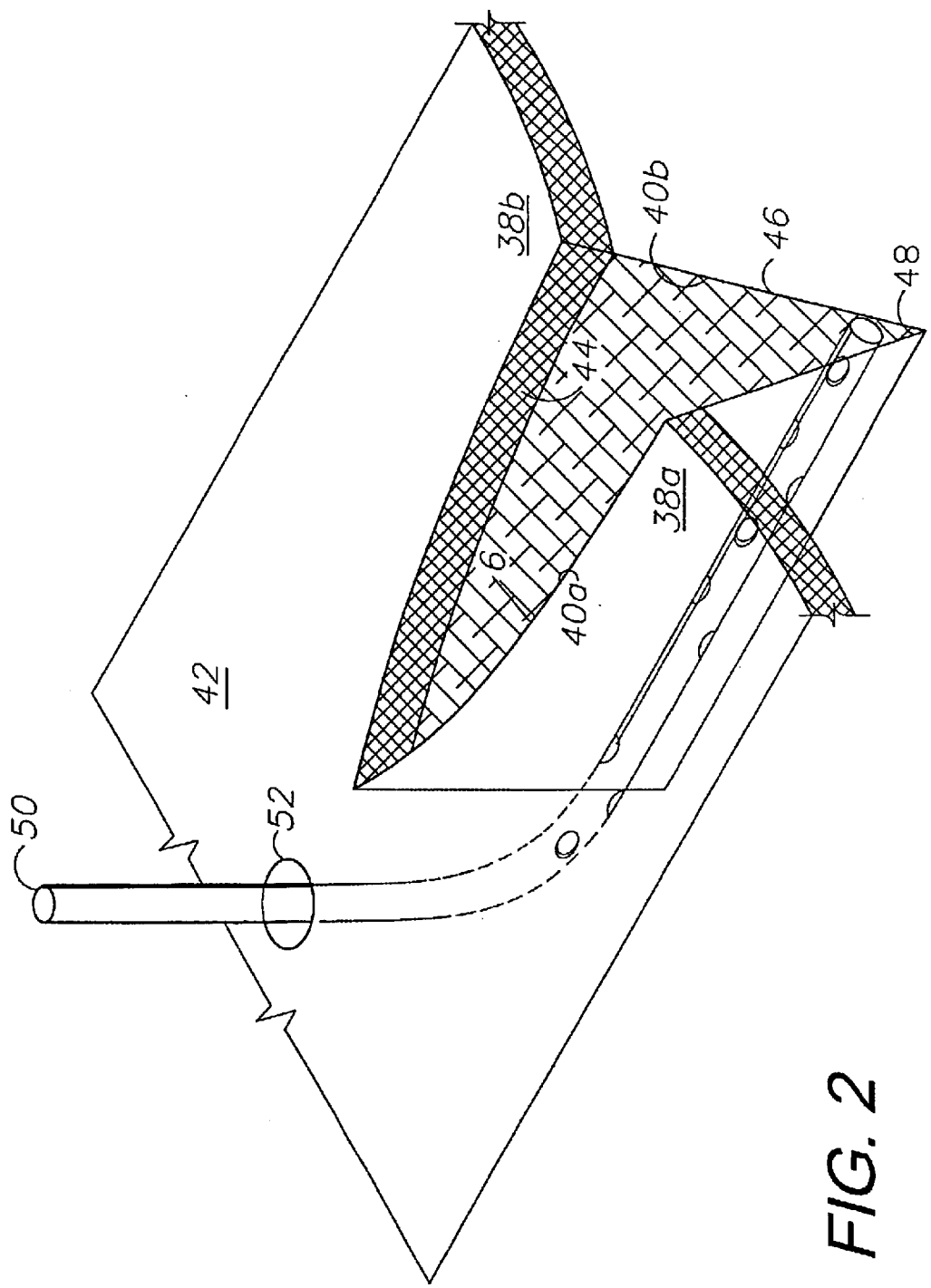
FIG. 2 is a perspective view of an incision tissue separation with a deep drain tube installed.

FIG. 2 shows an incision 6 forming first and second separated tissue portions 38a,b with incision edges 40a,b. The incision 6 extends from and is open at the skin 42, through the deep dermal layer 44 and the subcutaneous layer 46, to approximately the fascia 48. A deep drain tube 50 is placed in a lower part of the incision 6 and penetrates the skin 42 at an opening 52.

Figure 3:
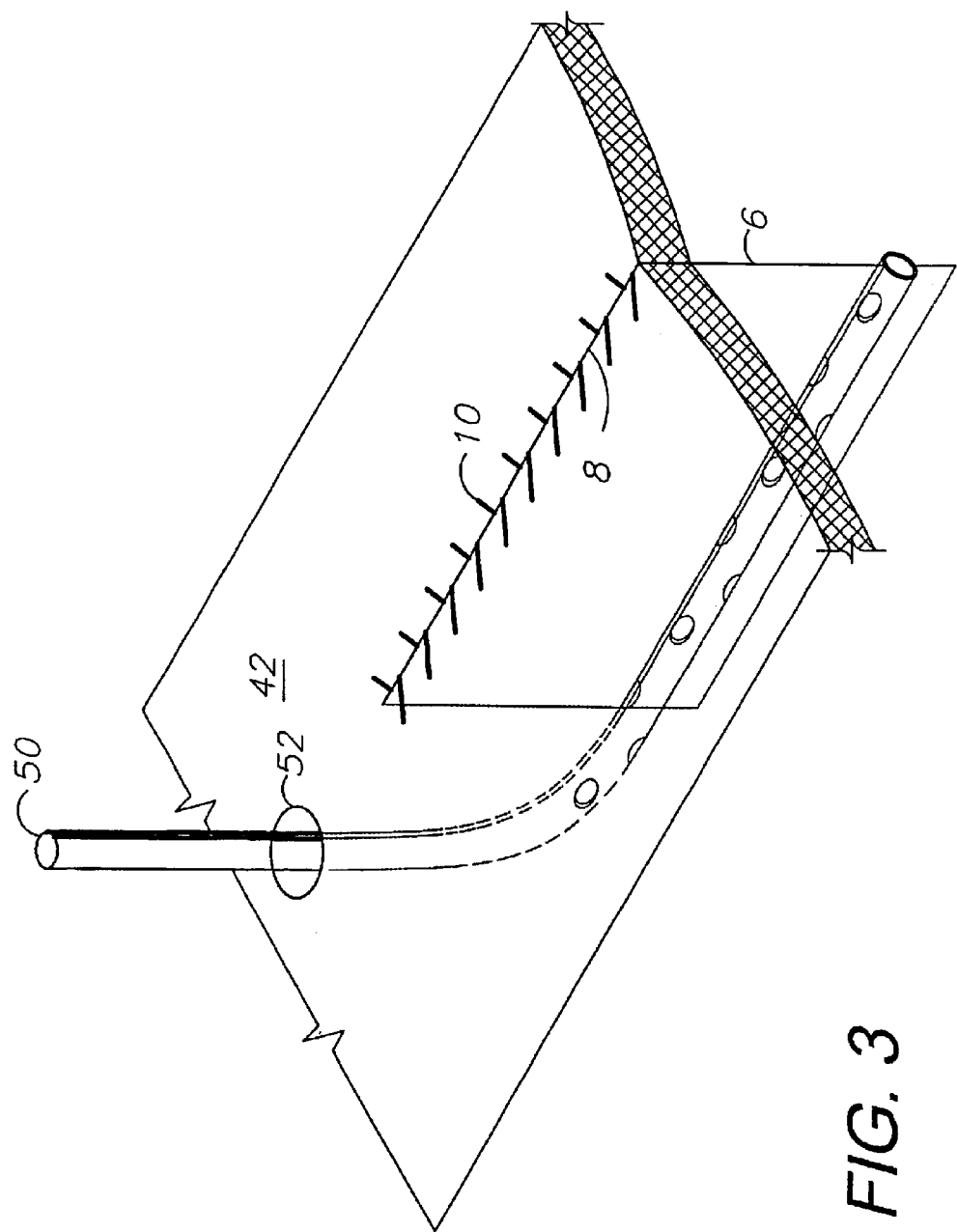
FIG. 3 is a perspective view thereof, showing the separated tissue sutured together at the skin.
Figure 4:
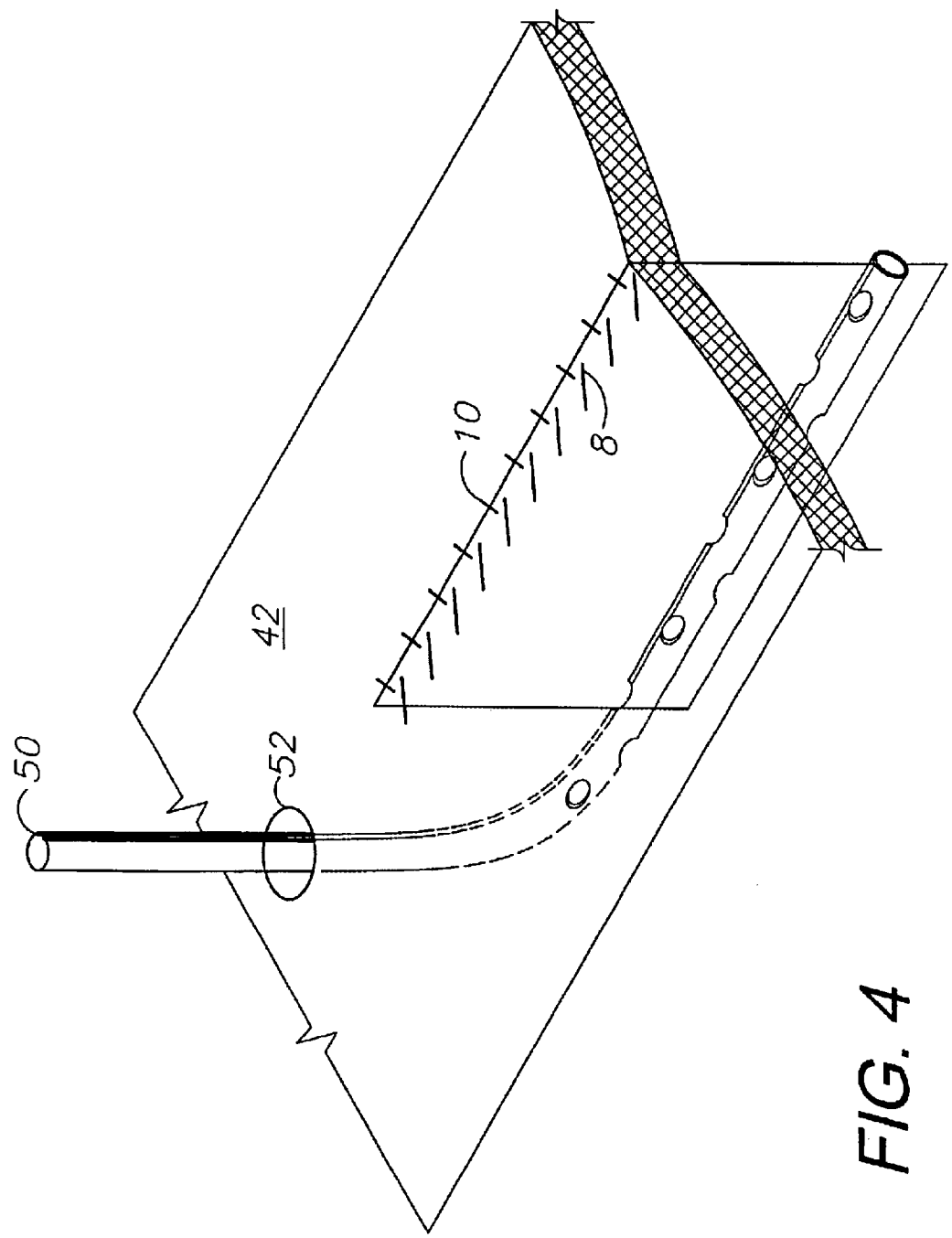
FIG. 4 is a perspective view thereof, showing the separated tissue sutured together at the deep dermal layer below the skin surface.

FIG. 3 shows the incision edges 40a,b secured together by sutures 54 forming a stitch line 56 at the skin surface 42. As an alternative to sutures 54, various other medical fasteners, such as staples, can be used. FIG. 4 shows sutures 55 placed in the deep dermal layer 44 below the skin surface 42.

Figure 5:
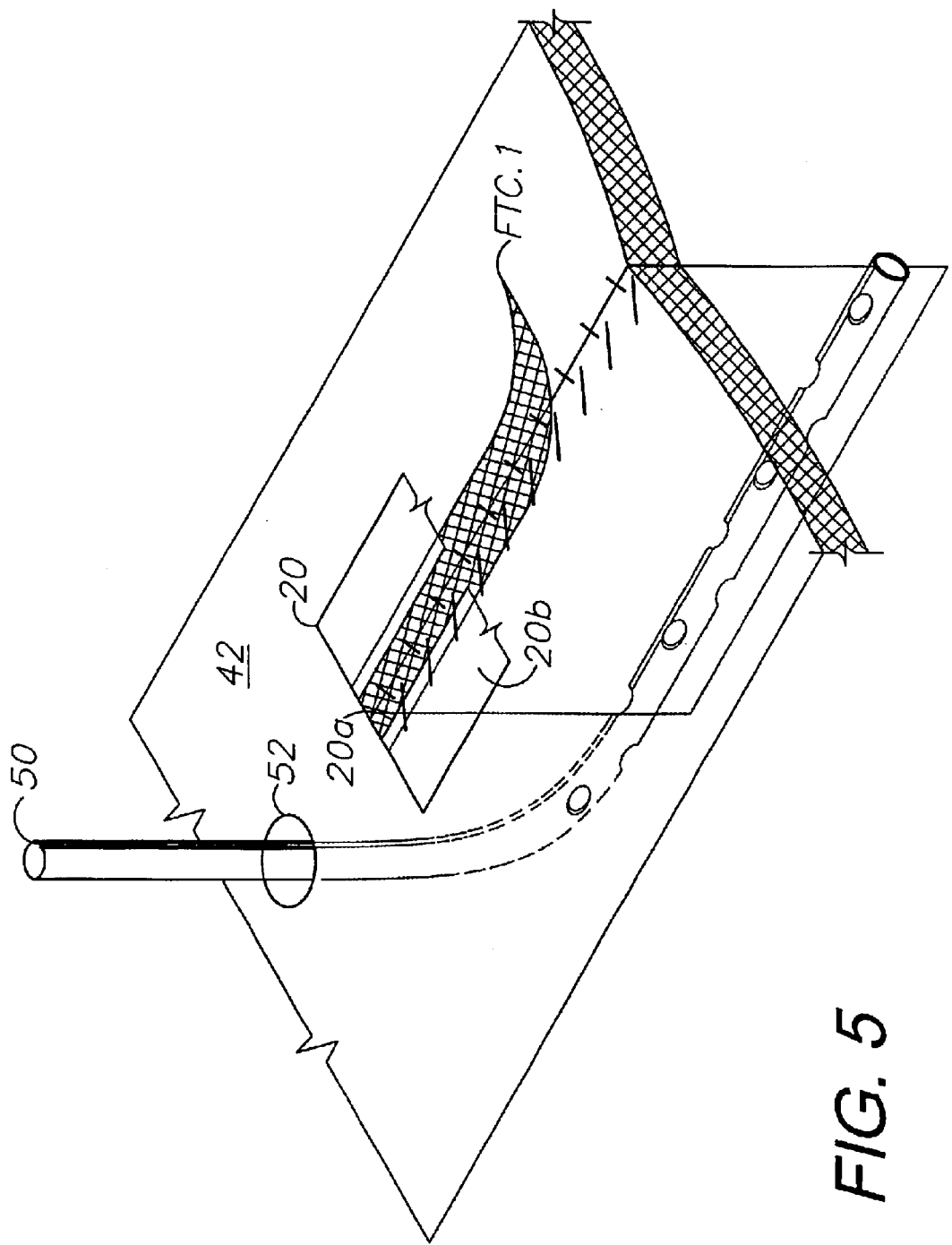
FIG. 5 is a perspective view thereof, showing a rayon strip primary fluid transfer component (FTC.1) and an underdrape being placed on the stitch line.
Figure 6:
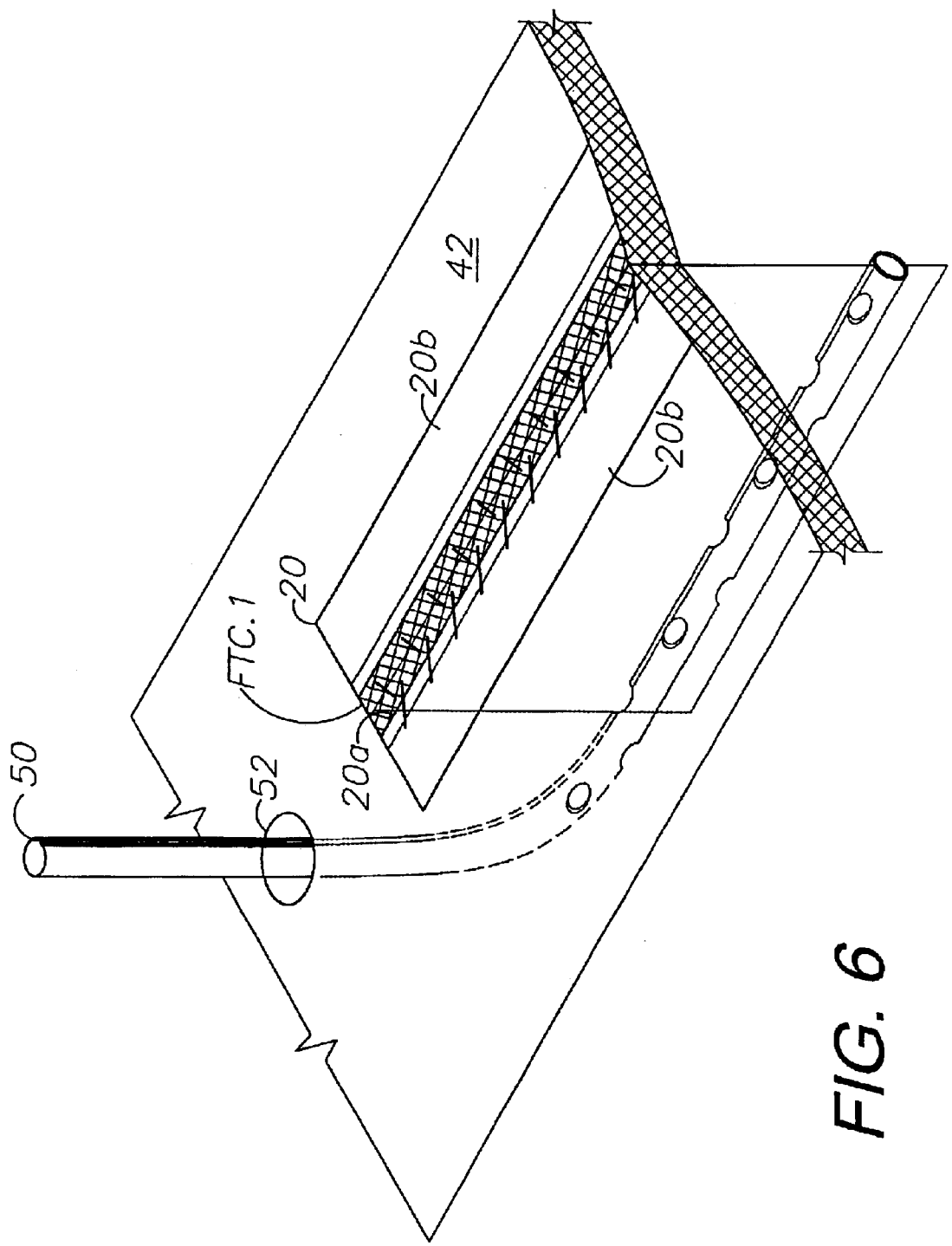
FIG. 6 is a perspective view thereof, showing FTC.1 and the underdrape in place on the stitch line.

FIG. 5 shows application of FTC.1 on top of the stitch line 8. FTC.1 preferably comprises a suitable porous wicking material, such as rayon, which is well-suited for wicking the fluid that exudes along the stitch line 8. Rayon also tends to dry relatively quickly, and thus efficiently transfers fluid therethrough. The underdrape 20 is placed over FTC.1 and the adjacent skin surface 42. Its slot 20a is generally centered along the centerline of FTC.1 and directly above the stitch line 8. FTC.1 and the underdrape 20 can be preassembled in a roll or some other suitable configuration adapted to facilitate placement on the stitch line 8 in any desired length. FIG. 6 shows FTC.1 and the underdrape 20 in place.

Figure 7:
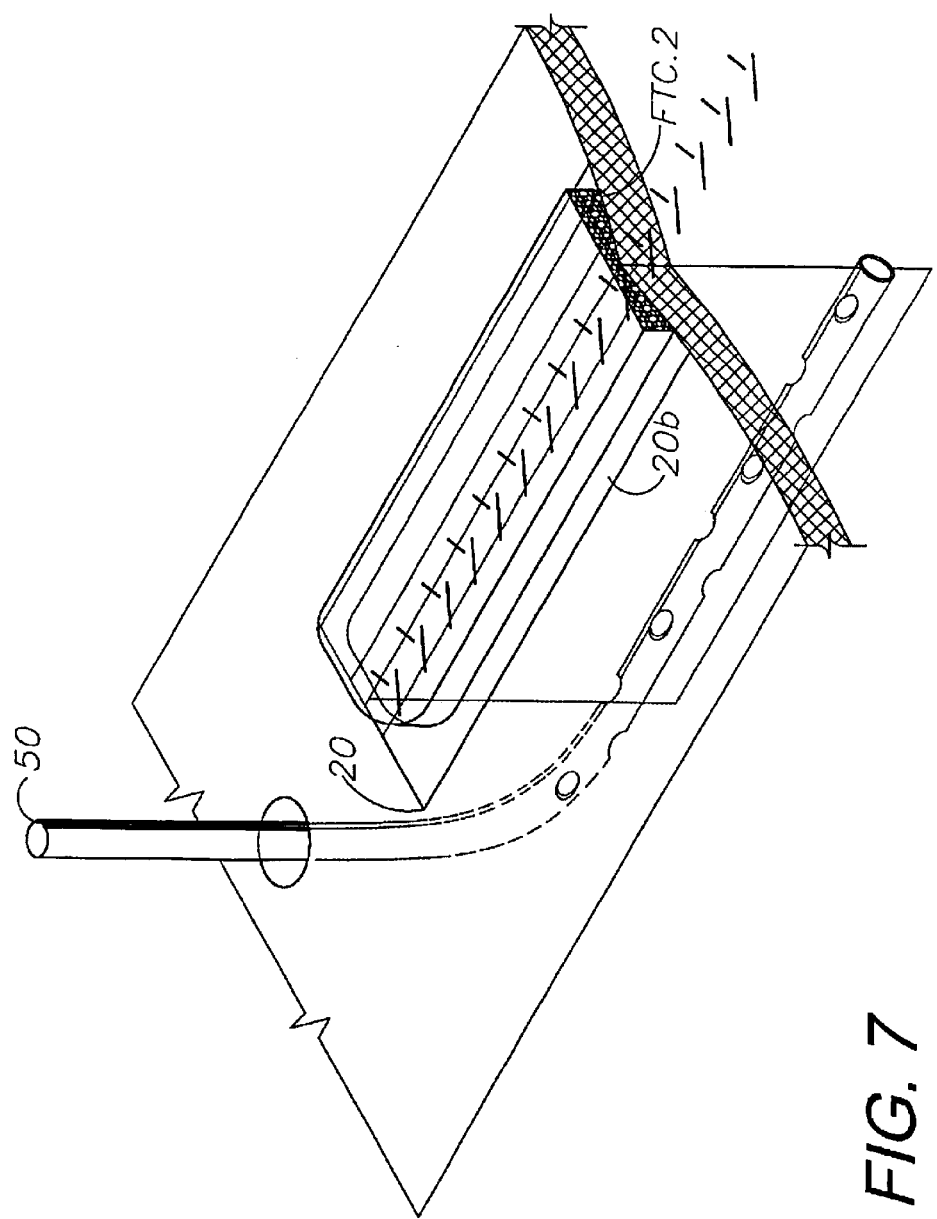
FIG. 7 is a perspective view thereof, showing a secondary fluid transfer component (FTC.2) in place.

The secondary fluid transfer component FTC.2 is shown installed in FIG. 7. It preferably comprises a suitable hydrophobic foam material, such as polyurethane ether (PUE), which comprises a reticulated, lattice-like (foam) material capable of being collapsed by vacuum force (negative pressure) in order to exert positive "shrink-wrap" type compression on skin surface and still maintain channels that allow passage of fluid. As shown, its footprint is slightly smaller than that of the underdrape 20, thus providing an underdrape margin 20b. The wicking layer of FTC.1 can, as an alternative, be sized equal to or almost equal to the footprint of FTC.2. This configuration lends itself to pre-fabrication as an individual, pre-assembled pad that can be employed by simply removing a releasing layer backing from an adhesive lined underdrape. This configuration also lends itself to easy total removal and replacement of the central part of the assembly without removing drape already adhered to skin if removal and replacement is the desired clinical option rather then staged removal or prolonged single application.

Figure 8:
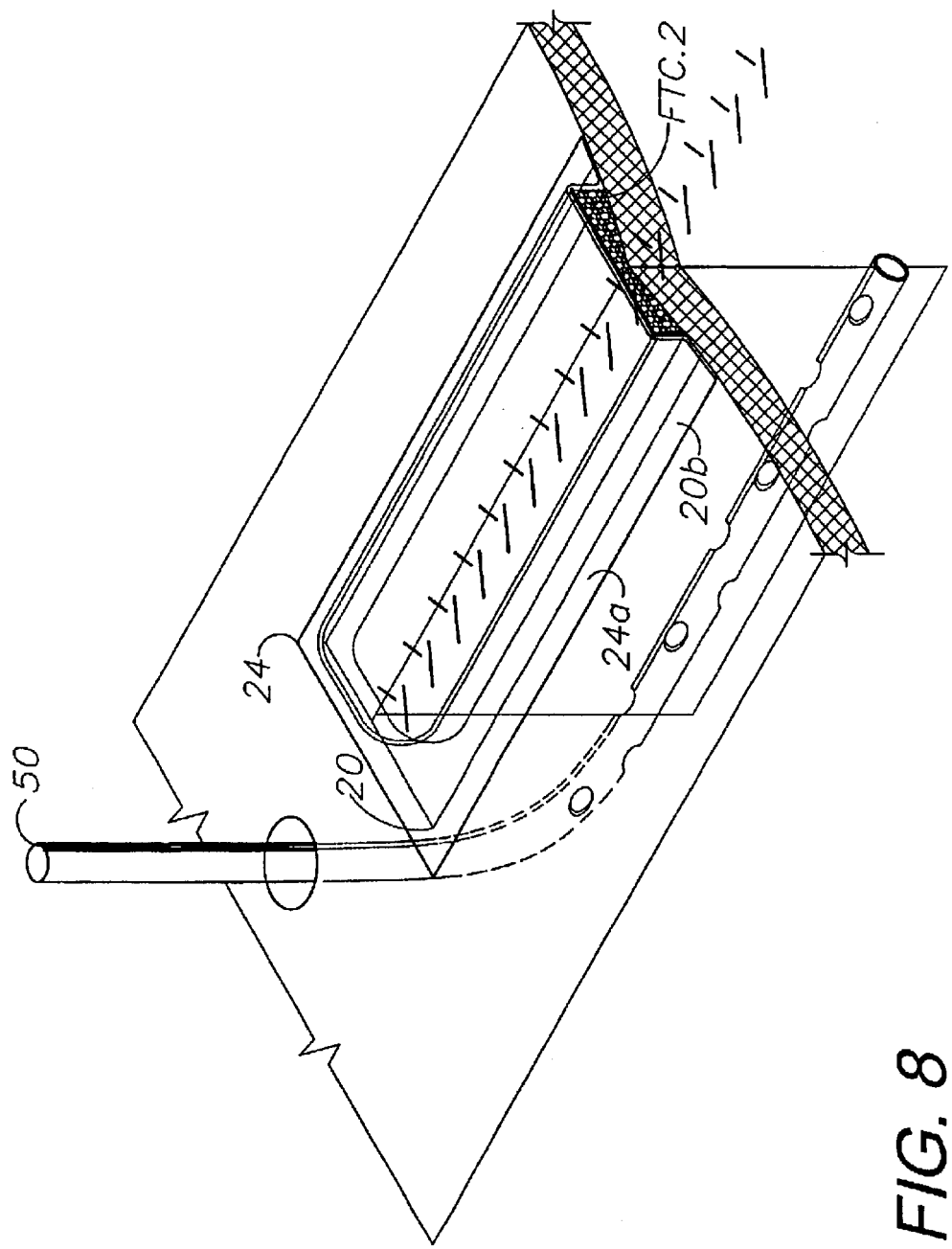
FIG. 8 is a perspective view thereof, showing an overdrape in place.
Figure 9:
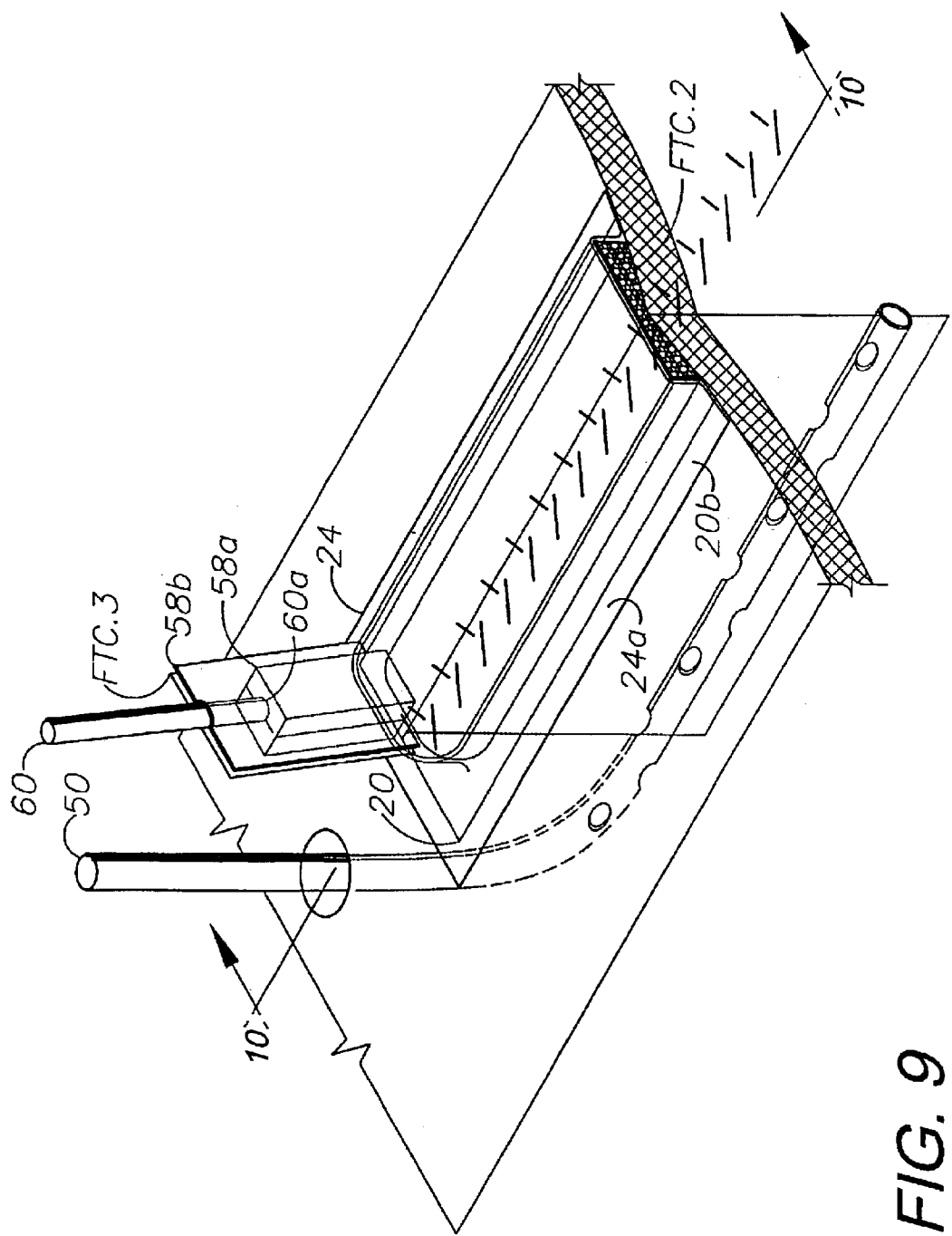
FIG. 9 is a perspective view thereof, showing a connecting fluid transfer component (FTC.3) in place for connecting the system to a negative pressure source.

FIG. 8 shows the overdrape 24 applied over FTC.2 and the underdrape 20, with a margin 24a extending beyond the underdrape margin 22b and contacting the patient's skin surface (dermis) 42. FIGS. 9 and 10 show a patch connector 58 mounted on FTC.2 and comprising a hydrophobic foam (PUE) material core 58a sandwiched between drape layers 58b. A vacuum drain tube 60 includes an inlet end 60a embedded in the foam core 58a and extends between the drape layers 58b to an outlet end 60b connected to the surface drainage negative pressure source 28.

Figure 11A:
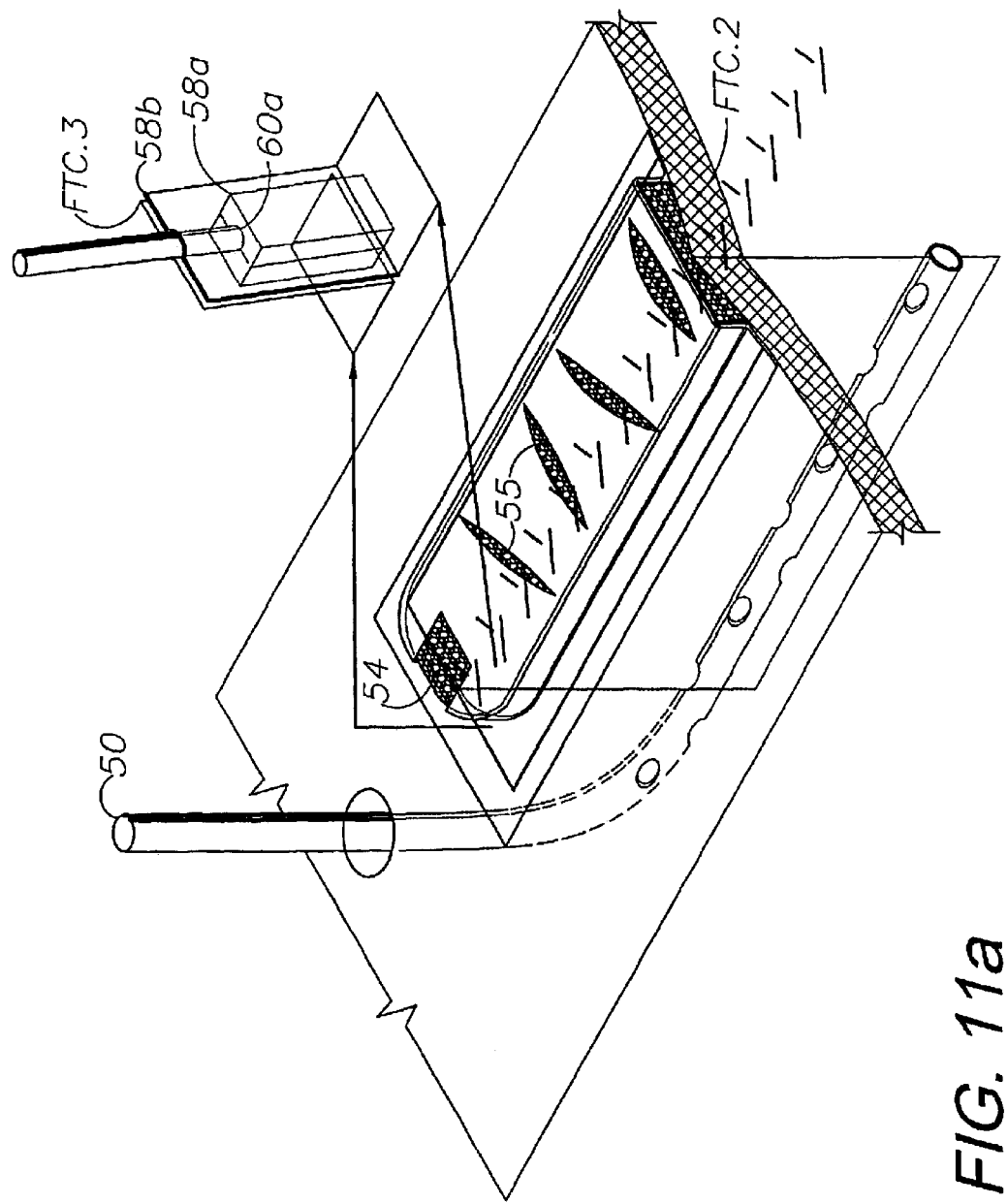
FIG. 11a is a perspective view thereof, showing FTC.3 removed and the overdrape scored for ventilation.

FIG. 11a shows FTC.3 removed, e.g. by cutting away portions of the overdrape 24 to provide an overdrape opening 54. In addition, the overdrape 24 can be slit at 55 to further ventilate FTC.2. Draining FTC.2 under negative pressure, and further drying it with air circulation (FIG. 11a) can provide significant healing advantages by reducing the growth of various microbes requiring moist environments in FTC.2. Such microbes and various toxins produced thereby can thus be evaporated, neutralized and otherwise prevented from reentering the patient. Microbe control can also be accomplished by introducing antiseptics in and irrigating various components of the patient interface 12, including the drapes 20, 24; FTC.1; FTC.2; and FTC.3.

Figure 11B:
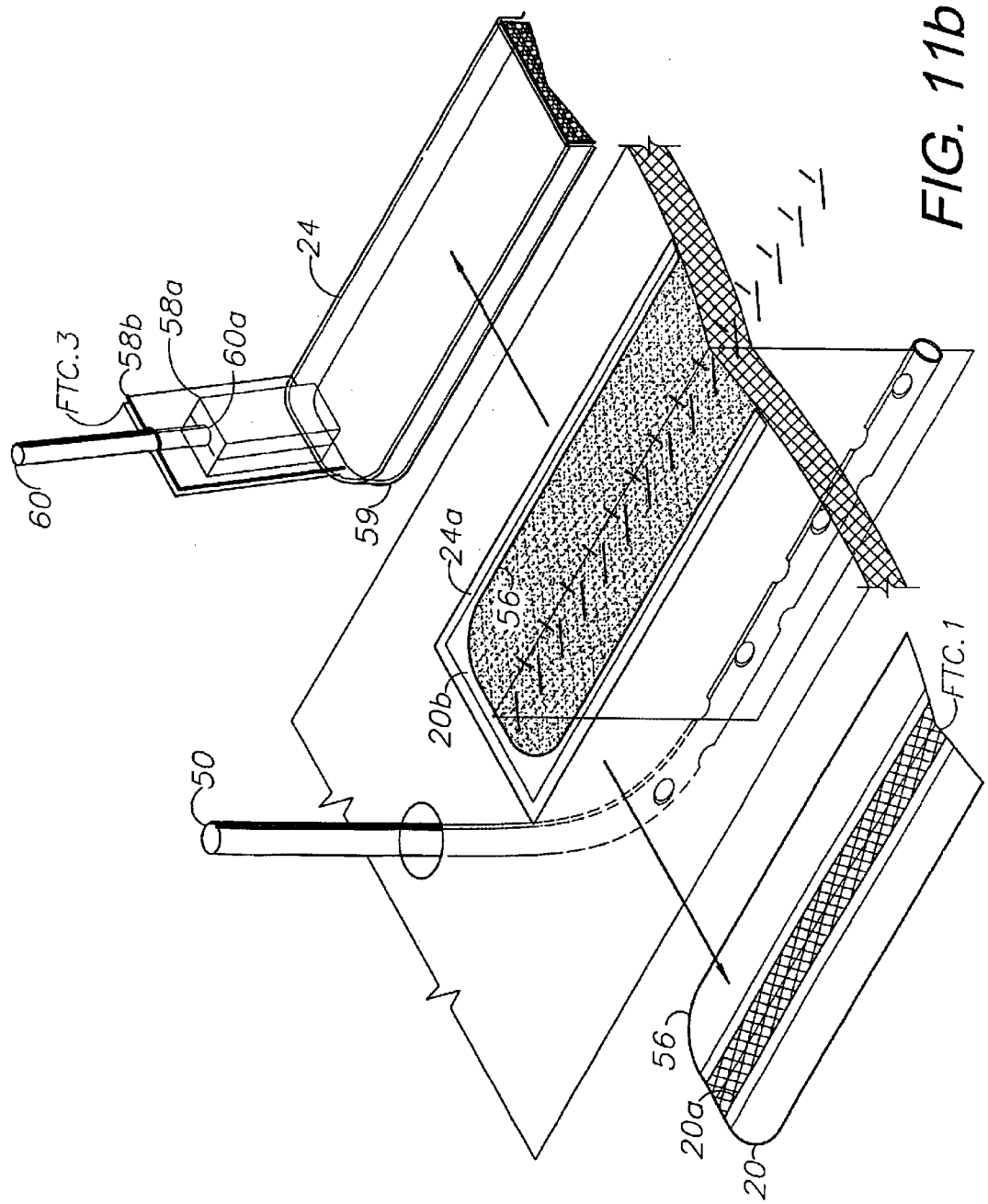
FIG. 11b is a perspective view thereof, showing the patient interface removed along a perforated tear line in the underdrape and a slit line in the overdrape.
Figure 12A:
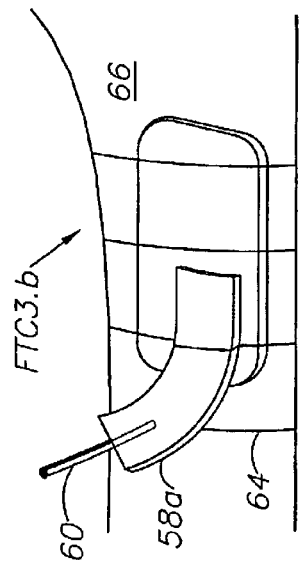
FIGS. 12a–d show alternative embodiment elbow connecting devices FTC.3a–d respectively.
Figure 12B:
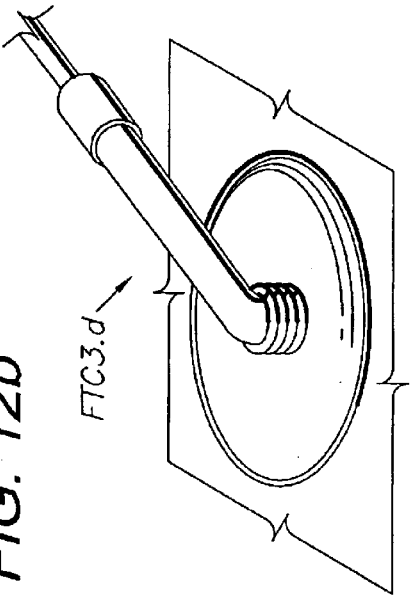
Figure 12C:
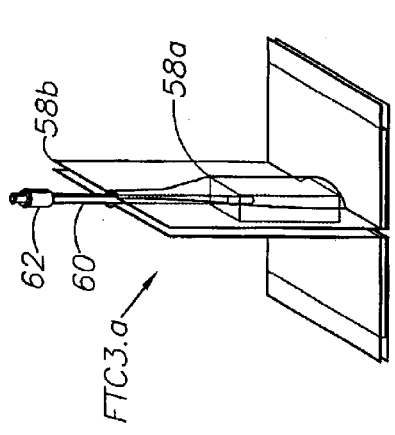
Figure 12D:
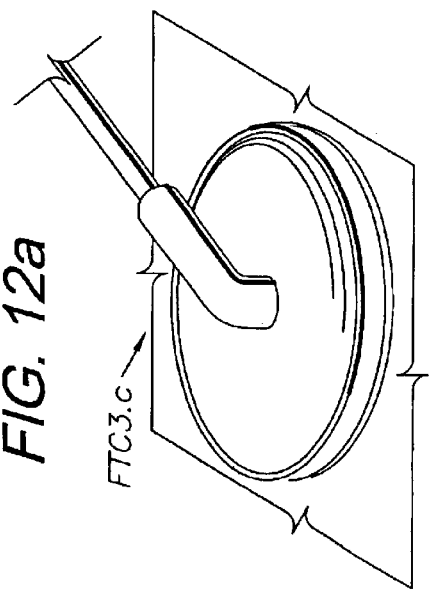

FIG. 11b shows the patient interface 12 removed along underdrape perforated tear lines 56 and slit lines 59 in overdrape 24. It will be appreciated that substantially the entire patient interface 12, except for underdrape and overdrape margins 20b, 24a can thus be removed to provide access to the stitch line 8 and the dermis 42 for visual inspection, evaluation, cleaning, stitch removal, dressing change (e.g., with prepackaged patient interface 12a as shown in FIG. 11c), consideration of further treatment options, etc. For example, the overdrape 24 can be slit to around the perimeter or footprint of FTC.2 to permit removing the same. Preferably FTC.2 is easily releasable from the underdrape 20 and FTC.1 whereby FTC.2 can be grasped and lifted upwardly to facilitate running a scalpel through the overdrape 24 and into a separation between the underside of FTC.2 and the underdrape 20. The FTC.1 can then optionally be removed by tearing the underdrape 20 along its tear lines 56 and removing same as shown in FIG. 11b.

FIG. 11c shows a prepackaged patient interface 12a adapted for initial or "dressing change" application. Optionally, the rayon strip FTC.1 can have the same configuration or "footprint" as the foam sponge FTC.2, thus eliminating the underdrape 20. The prepackaged patient interface 12a can be sterilely packaged to facilitate placement directly on a stitch line 8. Alternatively, the patient interface components can be prepackaged individually or in suitable groups comprising subassemblies of the complete patient interface 12. For example, the underdrape/FTC.1 and the overdrape/FTC.2 subassemblies respectively can be prepackaged individually. Various sizes and component configurations of the patient interface can be prepackaged for application as indicated by particular patient conditions.

Preferably, certain sizes and configurations would tend to be relatively "universal" and thus applicable to particular medical procedures, such as TJRs, whereby patient interface inventory can be simplified. Alternatively, the individual components can be assembled in various sizes and configurations for "custom" applications.

FIGS. 12a–d show alternative connecting fluid transfer components FTC.3a–d for connecting FTC.2 to the surface drainage negative pressure source 28. FTC.3a (FIG. 12a) shows a patch connector with a similar construction to FTC.3 and adapted for placement at any location on the overdrape 24. FTC.3a is provided with a Leur lock connector 62. FTC.3b (FIG. 12b) comprises a strip of hydrophobic (PUE) foam material partially covered by an overdrape 64, which can be configured as a wrap around a patient's limb or extremity 66. FTC.3c (FIG. 12c) is an elbow-type connector. FTC.3d (FIG. 12d) is a bellows-type elbow connector, which is adapted to accommodate deflection of the vacuum drain tube 60.

FIGS. 12e,f show an alternative construction of FTC.2a with multiple, removable wedges 57 formed therein and adapted for accommodating articulation, such as joint flexure. The flexibility of FTC.2a can thus be considerably enhanced for purposes of patient comfort, mobility and flexibility. Such wedges can extend transversely and/or longitudinally with respect to FTC.2a. FTC.2a functions in a similar manner with and without the wedges 57 in place or removed.

FIG. 12g shows a modified patient interface 312 with the underdrape 20 placed below FTC.1. This configuration permits removing FTC.1 without disturbing the underdrape 20. FIG. 12h shows a further modified patient interface 412 with FTC.1 having the same configuration or footprint as FTC.2, whereby they can be fabricated and bonded together. In this configuration the underdrape 20 can be omitted.

III. Treatment Method

Figure 13A:
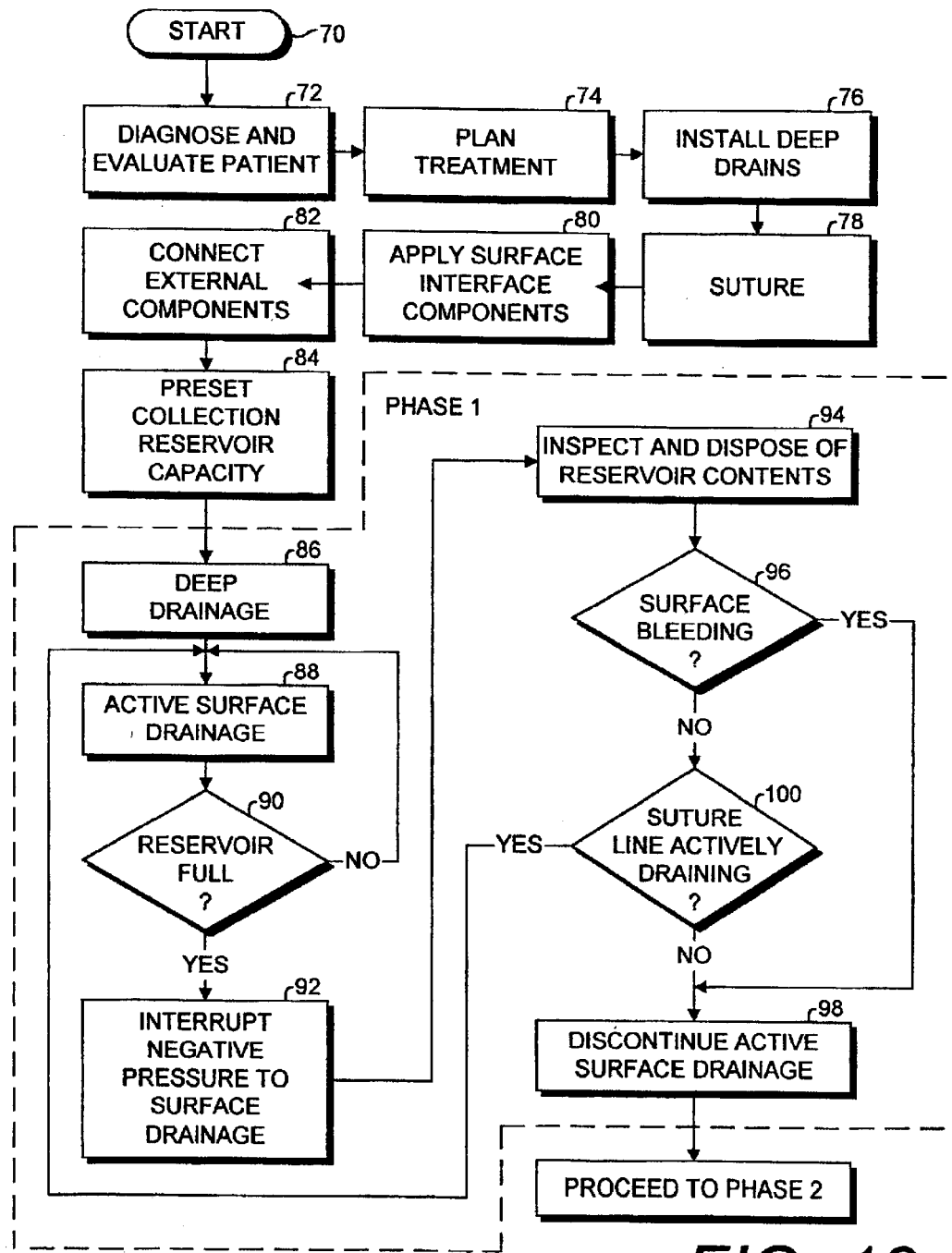
FIGS. 13a–c comprise a flowchart showing a tissue closure treatment method embodying the present invention.
Figure 13B:
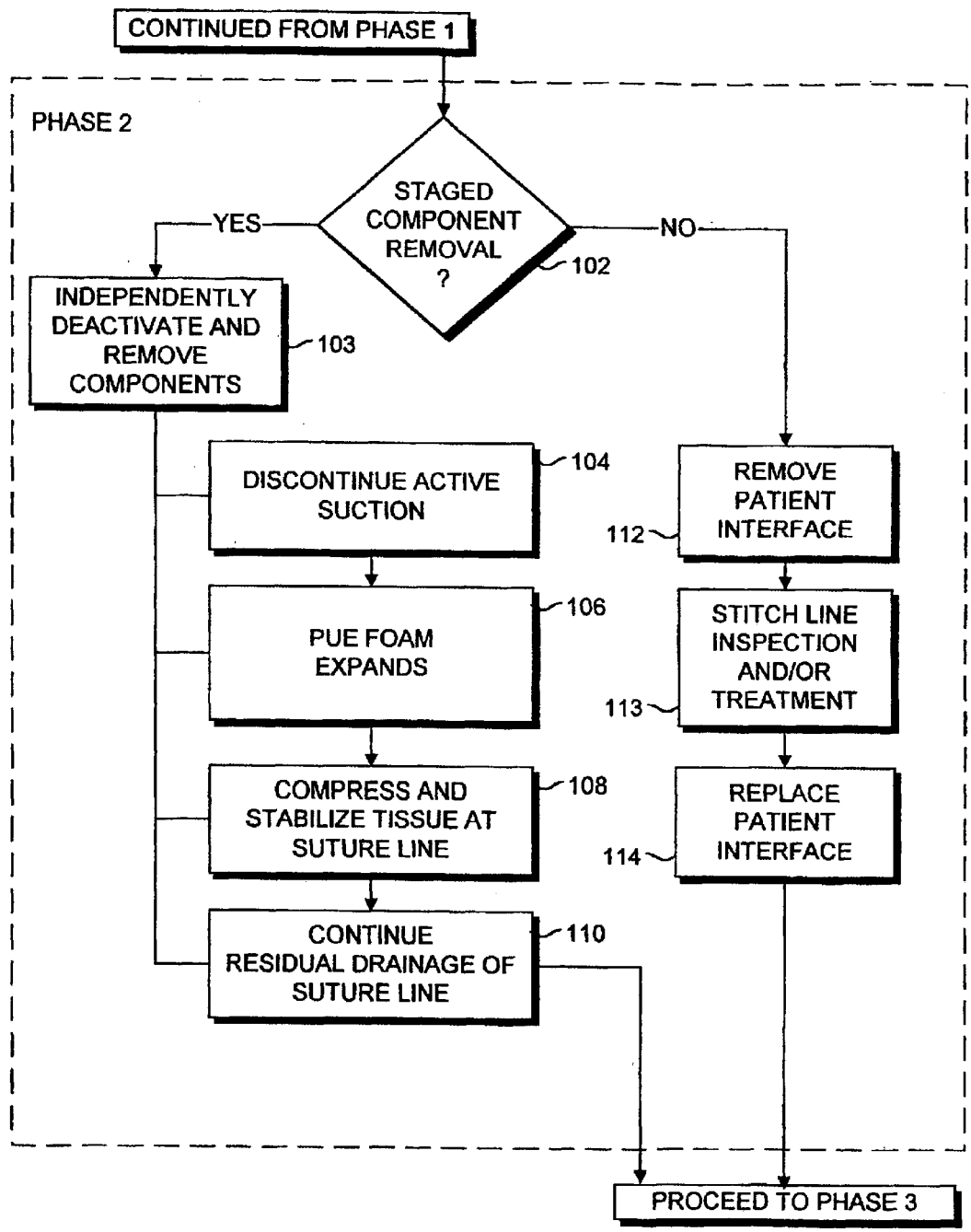
Figure 13C:
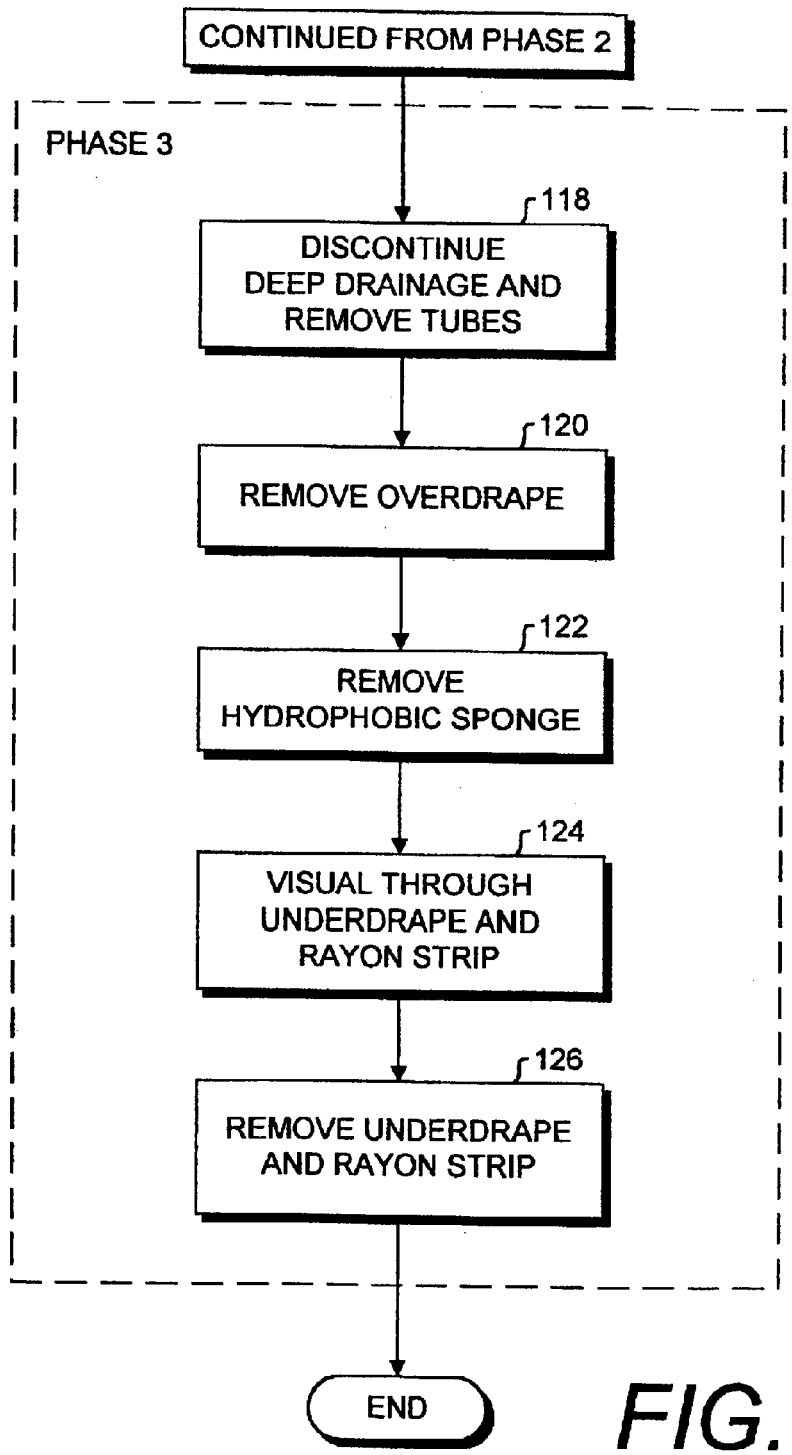

FIGS. 13a–c comprise a flowchart for a method embodying the present invention. From start 70 the method proceeds to patient diagnosis and evaluation at 72 and treatment plan at 74. Deep drains 14 are installed at 76 as necessary, and the incision is sutured at 78. Surface interface components 12 are applied at 80 and connected to the external components (i.e., negative pressure sources 15, 28) at 82. The collection reservoir capacity is preset at 84 based on such factors as nature of wound/incision, blood flow, etc.

Phase 1

Deep drainage occurs at 86 and active surface drainage occurs at 88, both being influenced by the negative pressure sources 15, 28. The negative pressure source 28 causes the PUE foam FTC.2 to partially collapse, which correspondingly draws down the overdrape 24 and exerts a positive, compressive force on the closed wound or incision 6. In the closed environment of the patient interface 12, such force is effectively limited to ambient atmosphere. This limiting control feature protects the patient from excessive force exerted by the patient interface 12. The steady force of up to one atmosphere applied across the closed wound or incision 6 functions similarly to a splint or plaster cast in controlling edema and promoting healing.

A "Reservoir Full" condition is detected at 90 and branches to an interrupt of the surface drainage negative pressure at 92, after which the reservoir contents are inspected and disposed of at 94. If surface bleeding is detected by visual inspection at decision box 96, the method branches to a "Discontinue Active Surface Drainage" step at 98. If the suture line is actively draining at decision box 100, the method loops to the active surface drainage step 88 and continues, otherwise active surface drainage discontinues at 98, i.e. when the wound/incision is neither bleeding nor exuding fluids.

Phase 1 is generally characterized by deep drainage (interactive or passive) and active surface drainage under the influence of manual or powered suction. The normal duration is approximately two to three days, during which time post-operative or post-trauma swelling normally reaches its maximum and begins to recede.

Phase 2

FIG. 13b shows Phase 2 commencing with a "Staged Component Removal?" decision box 102. An affirmative decision leads to independently deactivating and removing components at 103, including discontinuing active suction at 104, which transforms the hydrophobic PUE foam (FTC.2) internal pressure from negative to positive and allows the collapsed FTC.2 to reexpand at 106, potentially increasing surface composite pressure from ambient to positive. Preferably this transition occurs without applying undue pressure to the surface from the decompressed, expanding FTC.2. During Phase 1, negative pressure (i.e., suction/vacuum) tends to compress FTC.2 and correspondingly contracts the overdrape 24, adding to the compression exerted by FTC.2. When the application of negative pressure discontinues, either manually or automatically, FTC.2 re-expands against the constraints of the overdrape 24, and in an equal and opposite reaction presses against the skin 42, particularly along the stitch line 8. FTC.2 can thus automatically transform from ambient to positive pressure simply by discontinuing the application of the vacuum source.

The positive pressure exerted on the skin 42 continues to compress and stabilize tissue along the suture line 8 (step 108) in order to reduce swelling and cooperates with the operation of FTC.1 and FTC.2 to continue drainage by evaporation at the suture line 8 at step 110. A negative determination at decision box 102 leads to interface removal at 112 and, unless treatment is to be terminated, stitch line inspection and treatment at 113 and interface replacement at 114, which can involve all or part of the patient interface 12. The method then proceeds to Phase 3.

Phase 3

FIG. 13c shows Phase 3 of the treatment method wherein deep drainage is discontinued and the tube(s) is removed at 118. The overdrape 24 and FTC.2 are removed at 120, 122 respectively. The underdrape 20 and FTC.1 are preferably configured to permit visual inspection of the suture line 8 therethrough at 124. When the suture line 8 has closed sufficiently, the underdrape 20 and FTC.1 are removed at 126 and the treatment ends at 128. Alternatively and if indicated by the patient's condition, all or part of the interface 12 can be replaced in Phase 3 and treatment continued.

IV. Alternative Embodiment Tissue Closure System 202

Figure 14:
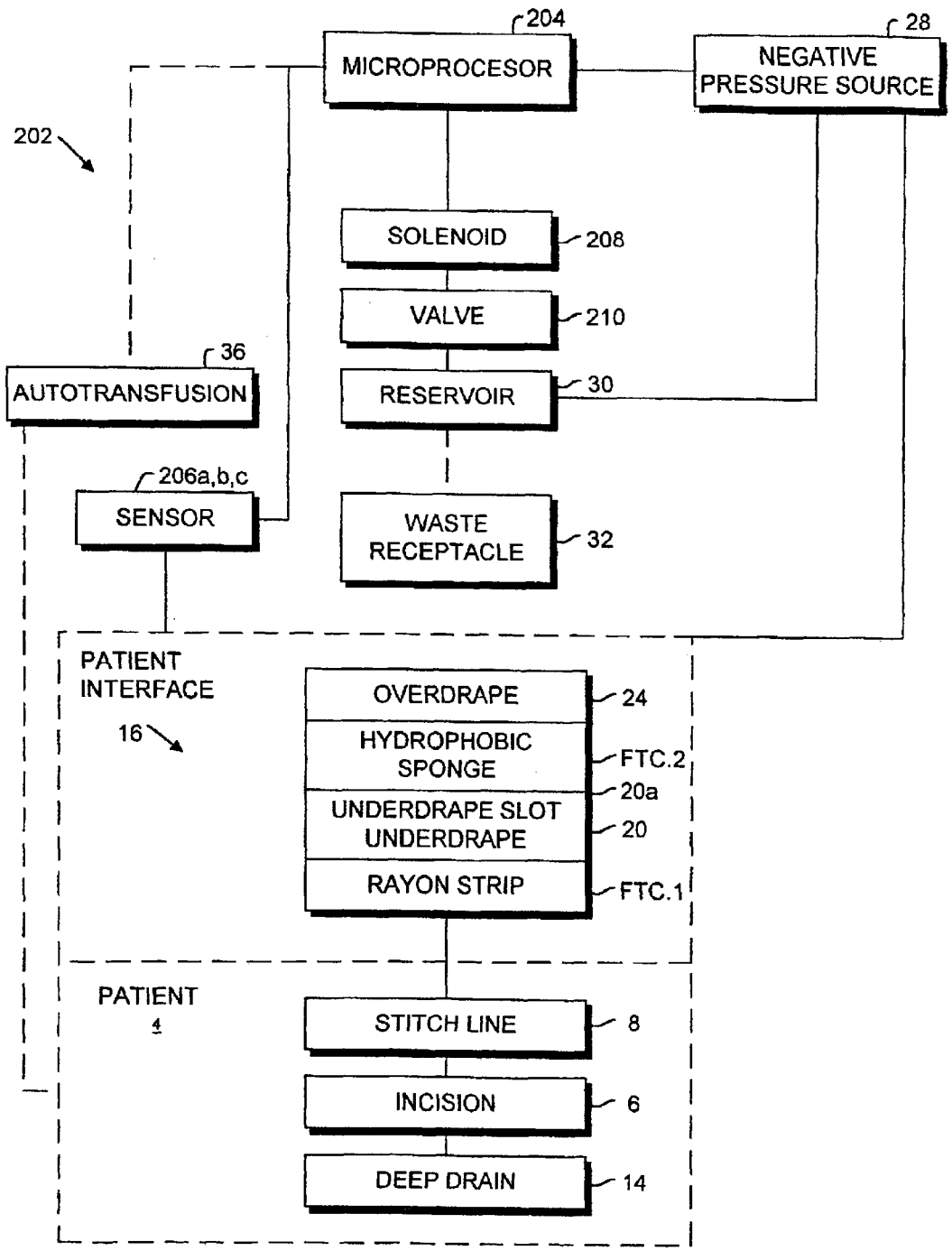
FIG. 14 is a schematic, block diagram of an automated tissue closure treatment system comprising an alternative embodiment of the present invention.

FIG. 14 schematically shows a tissue closure system 202 comprising an alternative embodiment of the present intention, which includes a microprocessor or controller 204, which can be connected to one or more sensors 206 coupled to the patient interface 12 for sensing various conditions associated with the patient 4. The microprocessor 204 can be programmed to operate a solenoid 208 coupled to a valve 210 associated with the reservoir 30 and controlling fluid flow induced by a negative pressure source 228 through its connection to the patient interface 12.

Figure 15:
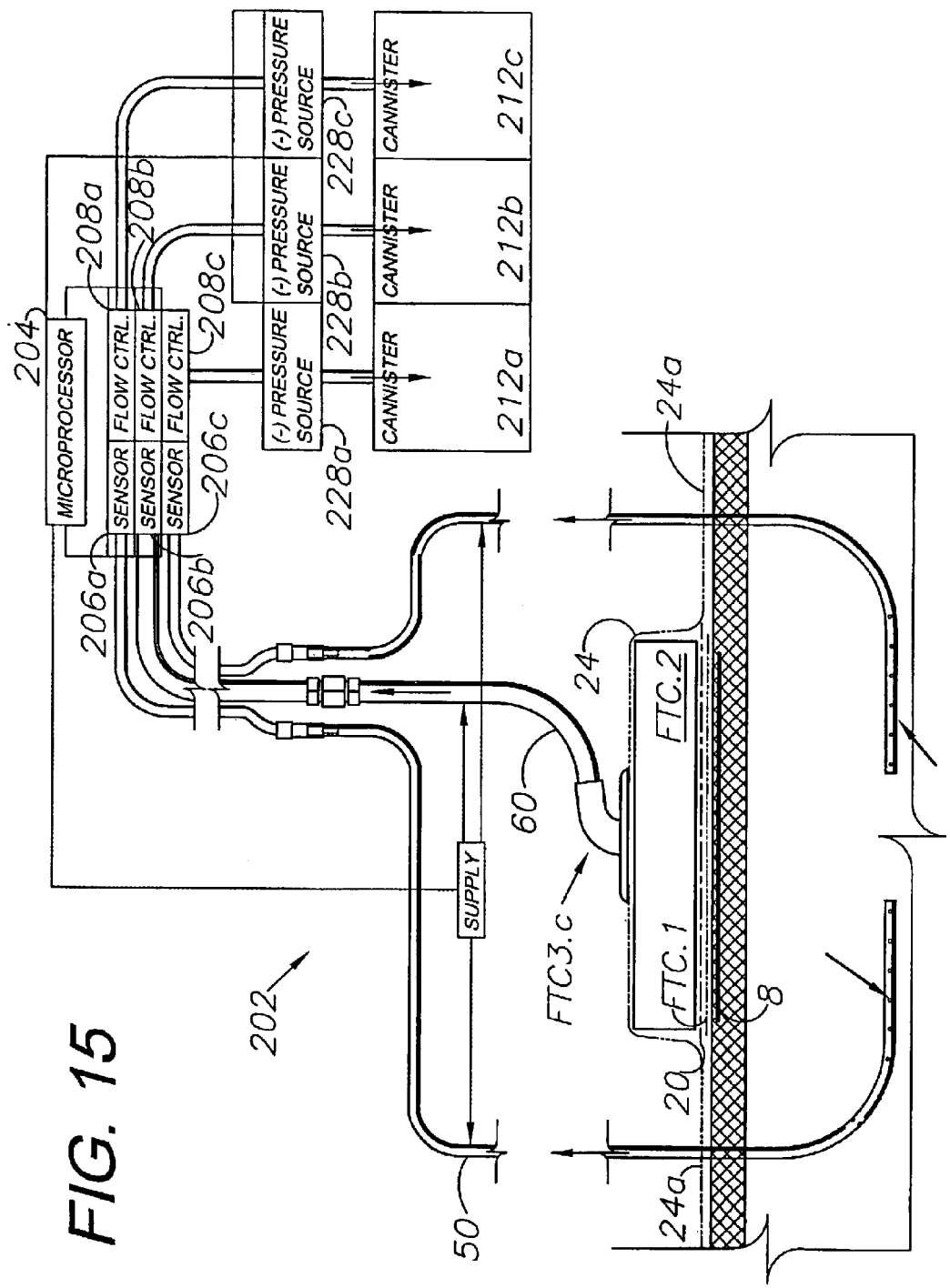
FIG. 15 is a cross-sectional view of the alternative embodiment automated tissue closure treatment system.

FIG. 15 shows the tissue closure system 202 with the microprocessor 204 connected to multiple sensors 206a,b,c each of which is associated with a flow control component, such as a valve, 210a,b,c respectively. Each flow control component 210a,b,c is associated with a respective negative pressure source 228a,b,c, which in turn controls fluid discharge into canisters or reservoirs 212a,b,c respectively. For example, the patient interface 12 can comprise an external patient interface 16 as described above and a pair of deep drainage tubes 50a,b. The patient interface 12 includes an optional supply component 214, which can comprise one or more fluid reservoirs, pumps (manual or powered) and associated controls, which can connect to the microprocessor 204 for system control. The supply component 214 optionally takes to one or more of the tubes 50, 60 for delivering fluid to the patient through the deep drainage tubes 50 or through the external patient interface 16. Such fluids can comprise, for example, antibiotics, and aesthetics, irrigating agents, growth factor, and any other fluid beneficial in promoting healing, countering infection and improving patient comfort.

Figure 16:
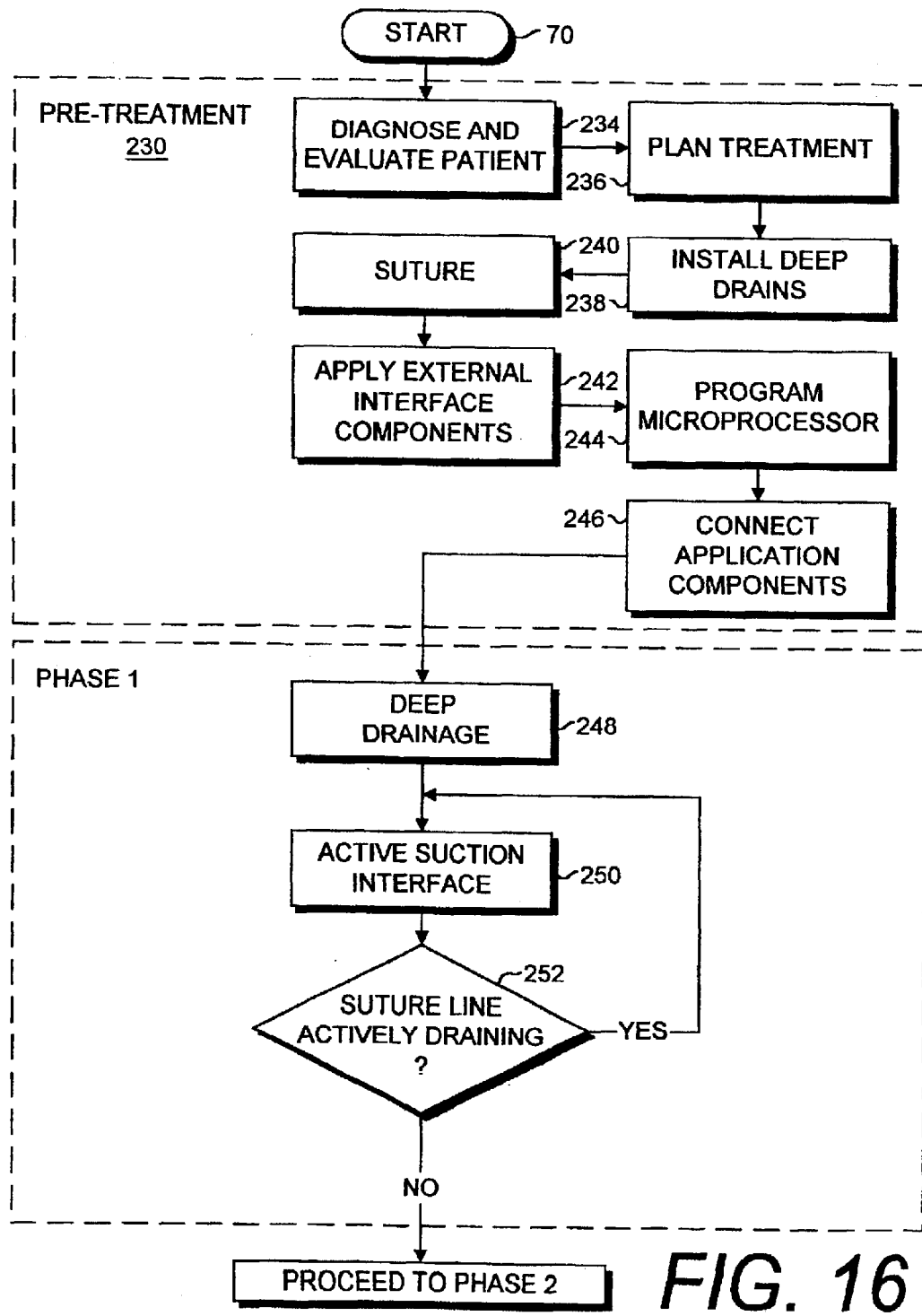
FIG. 16 is a partial flowchart of an alternative embodiment automated tissue closure treatment method embodying the present invention.

The methodology of the treatment with the alternative embodiment tissue closure system 202 is shown in FIG. 16 and generally involves modified pretreatment 230 and Phase 1 procedures. From "Start" the method proceeds to a diagnosis/evaluation step 234, a treatment plan step 236, deep drain installation 238, suturing at 240, external interface component application 242, microprocessor programming 244 and connection of the application components at 246, such as connection of the tubing. Phase 1 commences with deep drainage at 248, active suction interface at 250 and a "Suture Line Actively Draining?" decision box 252. If the suture line is actively draining, the method loops back to the active suction interface step 250, otherwise (negative determination at 252) it proceeds to Phase 2.

V. Applications

Without limitation on the generality of useful applications of the tissue closure systems 2 and 202 of the present invention, the following partial list represents potential patient conditions and procedures, which might indicate application of the present invention.

Over closed tissue separations, such as surgical incisions.

Over joints where the incision is subject to movement and stretching, such as arthrotomy, reconstructive proceedures, cosmetic procedures, flaps, scar revisions, Total Joint Replacement (TJR) procedures, i.e., hip, knee, elbow, shoulder and foot.

Any wound in an area of thick or unstable subcutaneous tissue, where splinting of skin and subcutaneous tissue might reduce dehiscence of deep sutures.

Wounds over reconstructive procedures in which irregular cavities are created. These include resection of tumors, implants, bone, and other tissues. Changes in length and geometry of limbs, and changes in size, position, and contour of bones and other deep structures.

Wounds in which elimination and prevention of dead space is important.

Treatment of hematomas and seromas.

Amputation stumps.

Abdominal, thoracic, flank, and other wounds in which splinting of the wound might assist closing and mobilizing the patient during the postoperative interval.

Wounds in areas of fragile or sensitive skin, where repeated removal and replacement of tape or other adhesives might produce pain, irritation, or blistering of skin in the vicinity of the wound. Also where dressing changes might produce shear or displacement of tissue so as to compromise primary wound healing.

Wounds in cases where the patient wishes to bathe before the skin has healed sufficiently to allow protection from contamination with bath or shower water.

Wounds subject to contamination with feces, urine, and other body fluids.

Pediatric, geriatric, psychiatric, and neurologic patients, and other patients likely to disturb dressings and wounds.

Patients with multiple consultants and care givers, where repeated inspection of the wound might compromise healing.

Deep closure and surface sutures and staples.

Any clean surgical or traumatic incision, open, or fully or partially closed by sutures, or where the skin edges can be apposed to a gap no wider than the width of the negative pressure zone of the dressing, i.e. where the maximum separation is less than or equal to the width of FTC.1 (rayon strip).

In cosmetic and reconstructive surgery, the systems and methods of the present invention can control and conceal the effects of early bleeding, exudation, ecchymosis, and edema of the wound.

In surgery on the limbs, where compression and drainage by this method might eliminate or reduce the need for circumferential compressive wrapping.

Tissue separations that are prone to protracted drainage, such as hip and knee incisions, and tissue separations in patients with health conditions, such as diabetes, that tend to inhibit healing. Shortened hospital stays might result from swelling reduction and control of drainage.

VI. Case Studies

General concept: sequential surface application of foam material (FTC.2) to surgical site and other wounds. Air-drying at the suture line is facilitated by the rayon strip (FTC.1).

Phase 1: deep drainage (drain tube(s)), active or passive; active suction applied to surface PUE foam (placed on top of surgical incision, drains bleeding and exudate from suture line); active suction compresses PUE foam, thus applying positive compression to the entire dissection field; adhesive-lined film underdrape with an MVTR of 3–800 on skin underlying PUE foam; rayon (or other suitable porous wicking material) strip on suture line; similar type of adhesive film overdrape (MVTR of 3–800) overlying PUE foam material.

Duration: approximately 2–3 days, i.e. effective time for active drainage from incision/stitch line to cease and for suture line to dry and heal.

Phase 2: Remove active suction by cutting off (elbow) connector and leave FTC.2 in place. Released from suction, FTC.2 expands against the overdrape and exerts positive pressure differential on the operation site. May maintain continued mild compression throughout Phase 2; residual drainage function through rayon strip and into FTC.2 provides continued drying of suture line. Deep drain tubes remain in place during Phase 2 for active deep drainage.

Duration: approximately three days, i.e. days 3–6 after operation.

Phase 3: remove overdrape and FTC.2; leave underdrape and rayon strip in place; visually observe wound healing progress; transparency desirable.

Duration: several (e.g., up to three) weeks.

Clinical trial confirmation: Closure of surgical site in upper chest area in patient with severe healing problems showed excellent results and rapid wound healing.

Subcuticular (subepidermal) sutures avoid conflict with rayon strip and need for early suture removal, or pressure on skin sutures beneath compressive black sponge.

Option: use pressure transducer for interface pressure mapping of wound site and automate control and monitor pressures, flow, etc.

Having thus described the invention, what is claimed as new and desired to be secured by Letters Patent is:

1. A system for compressively treating a closed wound or incision including first and second tissue portions connected by a suture line located at or near the skin surface, which system includes:

an external patient interface including a first fluid transfer component adapted for placement on the suture line, an underdrape adapted for placement on the skin surface in contact with the first fluid transfer component, a second fluid transfer component comprising a reticulated, compressible foam material placed on the first fluid transfer component in fluidic connection therewith and an overdrape placed over the second fluid transfer component and in contact with the skin surface;

a pressure source connected to the second fluid transfer component and adapted for applying a compressive pressure force thereto, said compressive force transferring from said second fluid transfer component to said closed wound or incision through said first fluid transfer component; and a control system adapted for selectively operating said pressure source in response to a condition associated with the treatment of the patient.

2. The system according to claim 1, which includes:
a third fluid transfer component connected to said second fluid transfer component and to said pressure source, said third fluid transfer component comprising a hydrophobic foam material core positioned within a membrane cover.

3. The system according to claim 1, which includes said underdrape having perforated tear lines facilitating the removal of said first fluid transfer component and a portion of said underdrape.

4. The system according to claim 1 wherein said second fluid transfer component includes multiple wedge-shaped portions adapted for selective removal for enhancing the flexibility of said second fluid transfer component.

5. The system according to claim 1, which includes a fluid supply subsystem including a fluid source adapted for connection to said external interface.

6. A method of compressively treating a closed wound or incision, which comprises the steps of:

applying a first fluid transfer component to intact skin adjacent to the closed wound or incision;

applying a second fluid transfer component to the first fluid transfer component;

draping said second fluid transfer component with an overdrape and securing same to the surrounding skin surface;

applying a vacuum force to said second fluid transfer component and thereby compressing same; and transferring a compressive force associated with said second fluid transfer component substantially exclusively to said intact skin adjacent to said closed wound or incision through said first fluid transfer component so as to apply compressive force to subdermal tissue adjacent to said closed wound or incision.

7. The method according to claim 6, which includes the additional steps of:

providing a deep drain tube in said closed wound or incision;

applying negative pressure to said deep drain tube; and draining said closed wound or incision through said deep drain tube.

8. The method according to claim 6, which includes the additional steps of:

providing a negative pressure source and producing said vacuum force therewith;

providing a controller;

connecting said controller to said negative pressure source and controlling same therewith in response to predetermined system operating conditions.

9. The method according to claim 8, which includes the additional steps of:

providing a fluid reservoir;

connecting said fluid reservoir to said second fluid transfer component through a drain tube;

draining fluid from said patient through said first and second fluid transfer components and said drain tube to said fluid reservoir;

providing said controller with a shut-off valve;

detecting a predetermined fluid volume in said reservoir; and activating said shut-off valve and thereby discontinuing the application of said vacuum force in response to said predetermined fluid level being detected in said reservoir.

10. The method according to claim 6, which includes the additional steps of:

partially collapsing said second fluid transfer component under the influence of said vacuum force;

discontinuing the application of said vacuum force;

reexpanding said second fluid transfer component against said overdrape;

constraining said second fluid transfer component with said overdrape; and exciting said compressive force through said reexpanded second fluid transfer component.

11. The method according to claim 6, which includes the additional steps of:

disconnecting said second fluid transfer component and at least a portion of said overdrape by slitting said overdrape around the perimeter of said second fluid transfer component; and visually inspecting said first fluid transfer component.

12. The method according to claim 11, which includes the additional step of changing said external interface by applying replacements thereof to the remaining margins of the previous underdrape and overdrape.

13. The method according claim 6, which includes additional steps of prepackaging said first and second fluid transfer components and said overdrape and changing the external interface by removing a previous external interface and applying said prepackaged fluid transfer components and overdrape in place thereof.

14. The method according claim 6, which includes additional steps of providing a fluid supply subsystem and fluidicaily connecting same to said second fluid transfer component and transferring fluid therefrom to said closed wound or incision through said first and second fluid transfer components.

15. A system for treating a closed wound or incision, which system comprises:

an external patient interface including a fluid transfer component adapted for transferring fluid from the closed wound or incision;

said external patient interface including an overdrape placed over said fluid transfer component in contact with a surrounding skin surface;

an underdrape placed under said fluid transfer component and adapted for engaging intact skin surface adjacent to said dosed wound or incision; and a pressure source connected to the fluid transfer component.

16. The system according to claim 15, which includes said fluid transfer component being adapted for transferring a compressive force to said closed wound or incision and said pressure source being adapted for exerting said compressive force.

17. The system according to claim 16, which includes said fluid transfer component comprising a first fluid transfer component, a second fluid transfer component and said compressive force being exerted by said pressure source on said second fluid transfer component and transferred to said closed wound or incision through said first fluid transfer component.

18. The system according to claim 15, which includes:
said fluid transfer component comprising a strip of wicking material.

19. The system according to claim 17, which includes:
said underdrape being placed between the first and second fluid transfer components.

20. The system according to claim 19, which includes:
said first fluid transfer component comprising a strip of rayon material; and
said uuderdrape including an opening through which said first fluid transfer component engages said second fluid transfer component.

21. The system according to claim 17, which includes said second fluid transfer component comprising a hydrophobic foam material.

22. The system according to claim 15, wherein said pressure source is connected to a fluid reservoir adapted to receive fluid from said system.

23. The system according to claim 22, which includes:
said pressure source being manually-operated.

24. The system according to claim 23, which includes:
said reservoir having a finite capacity; and
a shut-off valve associated with said reservoir and adapted for discontinuing fluid drainage upon said reservoir reaching a predetermined patient fluid volume.

25. A system for treating a closed wound or incision, which system comprises:
an external patient interface including a fluid transfer component adapted for transferring fluid from the closed wound or incision;
said external patient interface including an overdrape placed over said fluid transfer component in contact with a surrounding skin surface;
an underdrape placed under said fluid transfer component and adapted for engaging intact skin surface adjacent to said closed wound or incision;
said under drape including an opening through which said fluid transfer component is exposed and adapted for engaging intact skin surface adjacent to said closed wound or incision; and
a pressure source connected to the fluid transfer component.

26. A system for treating a closed wound or incision, which system comprises:
an external patient interface including a fluid transfer component adapted for transferring fluid from the closed wound or incision;
said external patient interface including an overdrape placed over said fluid transfer component in contact with a surrounding skin surface;

a pressure source connected to the fluid transfer component; and said first fluid transfer component being adapted for transferring a compressive force to intact skin surface adjacent to said closed wound or incision and said pressure source being adapted for exerting said compressive force.

27. The system according to claim 26, which includes:
said pressure source comprising a power-actuated vacuum source; and
a programmable controller connected to said vacuum source and adapted for preprogramming for controlling the operation of same.

28. The system according to claim 27, which includes:
a sensor associated with said patient interface and connected to said controller for controlling the operation of same; and
a valve associated with said pressure source and said controller and adapted for controlling fluid flow in response to a predetermined condition.

29. A system for treating a closed wound or incision, which system comprises:
an external patient interface including a first fluid transfer component and a second fluid transfer component placed on the first fluid transfer component in fluidic communication therewith, said fluid transfer components being adapted for transferring fluid from the closed wound or incision;
said external patient interface including an overdrape placed over said second fluid transfer component in contact with a surrounding skin surface;
a pressure source connected to the second fluid transfer component;
a deep drain located below the skin in said tissue separation; and
said deep drain being connected to said pressure source.

30. The system according claim 29, which includes said deep drain being connected to a common fluid reservoir with said external patient interface.

31. The system according to claim 29, which includes:
a deep drain negative pressure source connected to said deep drain; and
a deep drain fluid reservoir connected to said deep drain negative pressure source.

32. The system according to claim 29, which includes:
a third fluid transfer component removably mounted on said overdrape in fluidic communication with said second fluid transfer component; and
said deep drain including a drain tube connected to said third fluid transfer component and to said pressure source for draining said patient interface through said third fluid transfer component.

33. The system according to claim 32, wherein said third fluid transfer component comprises a hydrophobic foam material core exposed to said second fluid transfer component, and a membrane placed over said hydrophobic foam material component and adapted for mounting said third fluid transfer component on said overdrape.

34. The system according to claim 32, wherein said third fluid transfer component comprises an elbow adapted for placement on said overdrape over an opening in same.

35. A system for creating a closed wound or incision, which system comprises:

an external patient interface including a first fluid transfer component and a second fluid transfer component placed on the first fluid transfer component in fluidic communication therewith, said fluid transfer components being adapted for transferring fluid from the closed wound or incision;

said external patient interface including an overdrape placed over said second fluid transfer component in contact with a surrounding skin surface;

a pressure source connected to the second fluid transfer component; and said first fluid transfer component including multiple, removable pieces adapted for reconfiguring same for greater flexibility.

* * * * *

UNITED STATES PATENT AND TRADEMARK OFFICE
CERTIFICATE OF CORRECTION

PATENT NO. : 6,951,553 B2
DATED : October 4, 2005
INVENTOR(S) : Stephen K. Bubb et al.

It is certified that error appears in the above-identified patent and that said Letters Patent is hereby corrected as shown below:

Column 12,
Line 36, delete "exciting" and substitute -- exerting --.
Line 57, delete "fluidicaily" and substitute -- fluidically --.

Column 13,
Line 6, delete "dosed" and substitute -- closed --.

Column 15,
Line 4, delete "creating" and substitute -- treating --.

Signed and Sealed this

Twenty-eighth Day of February, 2006

JON W. DUDAS
*Director of the United States Patent and Trademark Office*